United States Patent
Vander Poorten et al.

(10) Patent No.: US 10,322,514 B2
(45) Date of Patent: Jun. 18, 2019

(54) APPARATUS FOR GENERATING MOTION AROUND A REMOTE CENTRE OF MOTION

(71) Applicant: KATHOLIEKE UNIVERSITEIT LEUVEN, Leuven (BE)

(72) Inventors: Emmanuel Vander Poorten, Mechelen (BE); Andy Gijbels, Paal (BE); Niels Wouters, Alken (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 390 days.

(21) Appl. No.: 14/760,396

(22) PCT Filed: Jan. 13, 2014

(86) PCT No.: PCT/EP2014/050513
§ 371 (c)(1),
(2) Date: Jul. 10, 2015

(87) PCT Pub. No.: WO2014/108545
PCT Pub. Date: Jul. 17, 2014

(65) Prior Publication Data
US 2015/0351857 A1     Dec. 10, 2015

Related U.S. Application Data

(60) Provisional application No. 61/751,781, filed on Jan. 11, 2013.

(30) Foreign Application Priority Data

Jan. 11, 2013   (GB) .................................. 1300490.8

(51) Int. Cl.
*B25J 9/10*      (2006.01)
*B25J 18/00*     (2006.01)
(Continued)

(52) U.S. Cl.
CPC ............. *B25J 18/007* (2013.01); *A61B 34/30* (2016.02); *B25J 9/1065* (2013.01);
(Continued)

(58) Field of Classification Search
CPC ............................... B25J 18/007; B25J 9/1065
See application file for complete search history.

(56) References Cited

U.S. PATENT DOCUMENTS 5,397,323 A    3/1995   Taylor et al.
6,425,865 B1   7/2002   Salcudean et al.
(Continued)

FOREIGN PATENT DOCUMENTS

EP     1553887 B1      7/2005
WO     2004037103 A1   5/2004

OTHER PUBLICATIONS

International Search Report and the Written Opinion of the International Searching Authority from the European Patent Office in International Application No. PCT/EP2014/050513 dated Apr. 8, 2014.
(Continued)

*Primary Examiner* — William Kelleher
*Assistant Examiner* — Gregory T Prather
(74) *Attorney, Agent, or Firm* — The Marbury Law Group, PLLC

(57) ABSTRACT

Apparatus (10) for generating motion around a remote center of motion (RCM), comprising a distal link (L12) arranged to revolve about the remote center of motion and to translate through the remote center of motion, a proximal link (L10) arranged to revolve about a proximal center of motion (LCM), coupled to a base link (L1), through a rotational joint (150) and a sliding joint (181), a first mechanism comprising a first link (L9) pivotally coupled to the proximal link (L10) and to the distal link (L12) and
(Continued)

operable to transfer motion of the proximal link relative to the proximal center of motion to a motion of the distal link relative to the remote center of motion by maintaining a parallelogram (PAR1), and a second mechanism operable to move the first link with two degrees of freedom in a plane parallel to the plane of motion of the proximal link, characterized in that the second mechanism comprises one link or a serial connection of links (L4, L8, L3, L7, L2, L6) connecting the base link to the first link, configured to have an orientation of instant motion which is different from an orientation of instant motion of the proximal link (L10), relative to the base link.

23 Claims, 28 Drawing Sheets

(51) Int. Cl.
*A61B 34/30* (2016.01)
*A61B 90/50* (2016.01)

(52) U.S. Cl.
CPC ... *A61B 2034/302* (2016.02); *A61B 2034/305* (2016.02); *A61B 2090/506* (2016.02)

(56) References Cited

U.S. PATENT DOCUMENTS

| | | |
|---|---|---|
| 2006/0196299 A1 | 9/2006 | Taboada et al. |
| 2016/0067732 A1* | 3/2016 | Nakamura .......... B05B 13/0405 |
| | | 427/427.2 |
| 2017/0246743 A1* | 8/2017 | Swarup ................. B25J 18/007 |
| 2018/0214225 A1* | 8/2018 | Hourtash ............... B25J 18/007 |

OTHER PUBLICATIONS

Search Report under Section 17(5) from the IP Property Office in Application No. GB1300490.8 dated May 21, 2013.

* cited by examiner

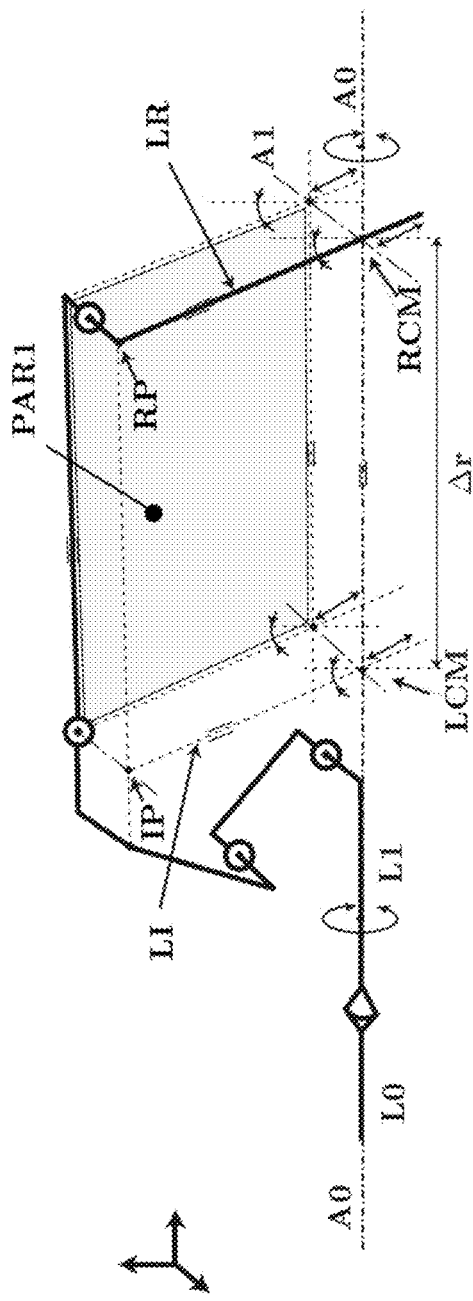
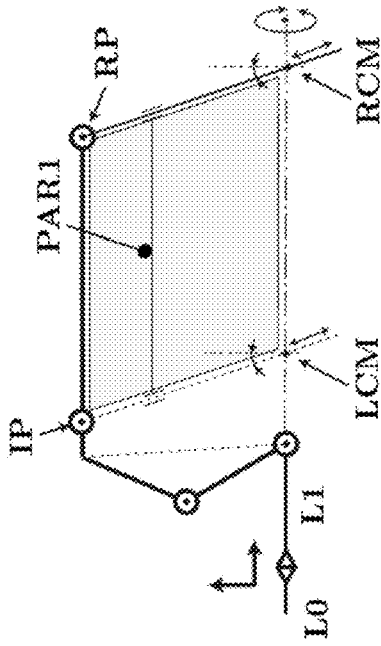
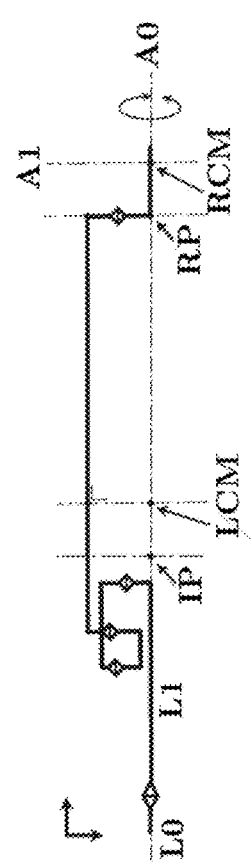
FIG 2A
FIG 2B
FIG 2C

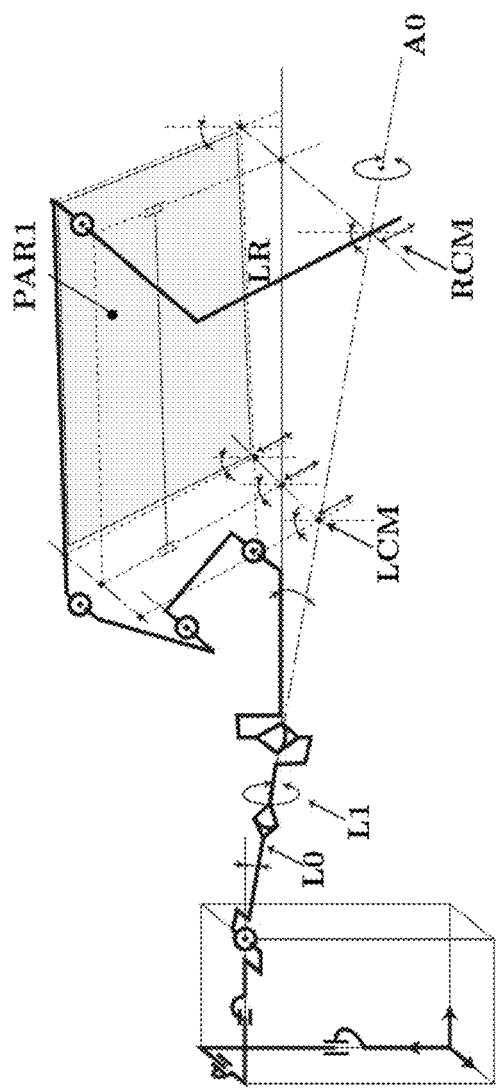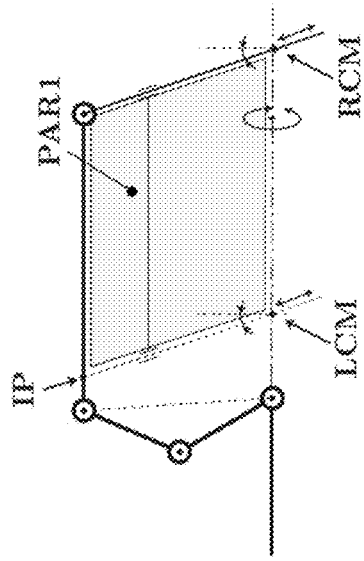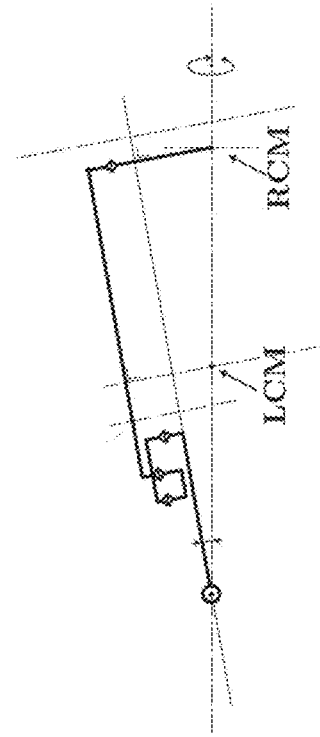
FIG 6A
FIG 6B
FIG 6C

APPARATUS FOR GENERATING MOTION AROUND A REMOTE CENTRE OF MOTION

TECHNICAL BACKGROUND

The present invention is related to the field of robotics, in particular to the field of robot assisted surgery. The invention is particularly related to manipulators for minimal invasive surgery (MIS) where instruments are to operate precisely inside the human body while only being granted limited access through small entry incisions and where low volume occupancy above the operation table is considered highly desirable.

In MIS, instruments can only reach the region of interest through the entry point into the body typically foreseen of a trocar. The trocar constraints the access to the region of interest, leaving only 4 degrees of freedom (DOF), compared to 6 DOF in open surgery, in the case rigid instruments are used. FIG. 1 shows the available degrees of freedom DOF1, DOF2, DOF3 and DOF4 consisting of three rotational DOFs (DOF1, DOF2 and DOF4) and one translational DOF (DOF3). The entry point is a pivotal point which causes motion reversal. The instrument tip moves in a direction opposite to the motion of the surgeon's hand. Further, the leverage of motion changes with increasing insertion depth. This makes accurate positioning more difficult at greater depth. The incision points do not provide stable pivots either. In order to achieve accurate instrument positioning, manipulators are used which physically constrain the instrument to pivot around a fixed point that coincides with the incision.

Several remote center of motion (RCM) mechanisms that orient an end-effector about two intersecting axes at a fixed geometric location in space have been developed in the past for use as manipulators in MIS, such as the ones described in U.S. Pat. Nos. 5,397,323, 5,817,084 and WO 2004/037103. When the RCM is aligned properly with the entry port into the body, the instrument can only pivot around the RCM point and is thus physically constrained and not able to exert large forces upon the body wall. Alternative systems e.g. applied to conventional serial or parallel robot mechanisms rely on software constraints to make the instrument pivot around the entry-point of the body. Such approach is often described as a 'virtual' or 'soft' RCM. Motion about an RCM is achieved by coordinated motions of multiple joints, many of which may be required to make fairly large motions in order to achieve relatively small tool reorientations. Such virtual RCM systems can be bulky and need to be sufficiently powerful to ensure good dynamic behaviour at the instrument. In case of failure it becomes difficult to guarantee patient safety, which makes them less suitable for MIS.

Apart from safety, sterilisability and reachable workspace inside the patient, accessibility and achievable precision form other crucial properties of instrument manipulators.

Since the majority of MIS interventions are conducted with multiple simultaneously handled instruments, it is necessary that instrument manipulators are compact and occupy as little as possible space above the patient. This is essential for finding configurations of instrument holders with non-overlapping workspace that can tackle various multi-instrument tasks. Also for cases where the workspace is shared with the surgeon, e.g. when some of the instruments are managed by the latter, the instrument manipulator should take in as few as possible not to hinder the surgeon. Furthermore, the space taken up by the instrument manipulator should be well-defined and predictable so that there is little room for surprises (surprising robot movements) and the surgeon can easily avoid collisions with the robot.

Traditional mechanisms that employ a combination of linkages and parallelograms to achieve a 'mechanical' RCM score better in terms of affordability and compactness. However, current mechanisms typically only support remote actuation of the distal two rotational degrees of freedom DOF1, DOF2. Such solutions make use of a translation stage located at the end-effector to provide the linear translation of the instrument along its axis through the insertion point, inwards and out-wards into the patient's body (translational degree of freedom DOF3). Often additional means to rotate the instrument about its axis (rotation degree of freedom DOF4) are additionally mounted on top of such stage. Such translation/rotation stages not only take in a lot of space above the patient, blocking the access and view of the surgeon or visualisation devices; they also present a relatively large mass at the robot's end-effector limiting the dynamic range. The stage and actuators form a variable load upon the lower elements of the kinematic chain; they jeopardize the achievable positioning accuracy, complicate the design of gravity compensation methods and further affect patient safety as actuators move in close vicinity to the patient. With stages it also becomes more difficult to guarantee safety, maintain sterility and so on.

Taylor (U.S. Pat. No. 5,397,323) describes an RCM-mechanism formed by a double set of parallelograms which features local actuation of the remote translational degree of freedom DOF3 (U.S. Pat. No. 5,397,323, FIG. 1D). The proposed approach relies on a pair of telescopic arms that form two opposite links of the first parallelogram at the mechanism's base. By extending or shortening both telescopic links in equal amounts, the parallelogram can be deformed into a larger or smaller parallelogram. As a result the instrument which is parallel to the respective telescopic arms will be displaced along its own axis passing through the remote center of motion and as such creating a translational degree of freedom DOF3.

For such method to work it is imperative that the telescopic arms move precisely and at all times in equal amounts, otherwise the RCM is lost. This can be achieved by employing two linear actuators that are controlled to move in a synchronous fashion at the cost of additional complexity, inertia and reduced reliability. An alternative exists in simply adding an extra connection bar between the telescopic arms to form an additional parallelogram over these arms. This parallelogram will carry the non-actuated telescopic arm along with the actuated one. However, when the angle between the parallelogram's links becomes 90 degrees, this parallelogram might transform and shift towards an isosceles prism configuration, in which case the RCM is not maintained either.

Methods to circumvent this safety problem are complex, bulky and/or affect the achievable positioning precision of the mechanism. For example, a possible solution presented in U.S. Pat. No. 5,397,323 FIG. 5 exists out of an additional mechanism that consists of a set of 5 bars and 6 additional pivot points. For the mechanism to work the lengths of 4 out of 5 bars must be exactly the same, the length of the fifth bar must perfectly match the length of the side of the main parallelogram. If this is not the case the mobility of the mechanism can be completely lost and the parallelogram will be unable to extend or retract. When adding play to the pivot points to relax these tight manufacturing constraints, the stability of the RCM point and the precision of instrument positioning suffers.

A second possible solution presented in U.S. Pat. No. 5,397,323, FIG. 6, provides in a pair of pulleys attached at the extremities of a common rigid bar, connected through a belt-like mechanisms. The bar and pulleys move over two rolling surfaces that slide along a pair of linear bearings. Two assumptions must be fulfilled for this system to work. Firstly, both pulleys are to roll without any slip over the rolling surfaces. If one relies on rolling friction and pre-tensions hereto the components to achieve sufficiently high friction, pre-tensioning should be designed for worst-case loading of the mechanism to prevent slip from occurring under all possible circumstances. Such methods will introduce additional friction into the mechanism, typically limiting the smoothness of motion of the mechanism and will require a substantial torque/force to get the system running. Depending on the friction it becomes difficult to allow small incremental motion. Also, if at some point slip did occur it is not straightforward to detect and rectify this. Alternative methods that would rely e.g. on rack-and-pinions or timing belts, must be designed to be free of play. Zero-backlash versions require precise manufacturing, are costly and add substantial amounts of friction. Secondly, the two pulleys must rotate at all times at exactly the same speed. This would again require high pre-tensioning of very stiff belts introducing additional friction, or the use of precision timing belts free of play.

While the abovementioned approaches aim to avoid the loss of the RCM caused by a shift from the corresponding parallelogram to an isosceles trapezoid, they may at the same time further reduce the achievable workspace of the mechanism due to internal collisions between the additional plurality of links.

In fact the workspace by the proposed solution is somewhat restricted even without above corrective means. Since the instrument axis and the telescopic arms from the driving parallelograms are always parallel for acute and/or obtuse instrument angles also the angles of the driving parallelograms will be acute and/or obtuse. Internal collisions between these parallelograms will prevent reaching such acute and/or obtuse orientations.

The same parallelism property also allows for limited room in optimizing dynamics, manipulability, gravity compensation mechanisms and the like. For example regarding gravity compensation the parallelism requires to compensate for often coinciding worst-case loadings at instrument and driving mechanisms. These compensation means are therefore typically larger than in cases where instrument axis and driving mechanism can have a different orientation.

Further, the transmission from the local to the remote site of the mechanism relies on two parallel connecting bars that move relatively with respect to each other. Therefore the overall connection between local and remote site is rather bulky. It becomes also difficult to realize longer distances between local and remote site as this requires the manufacturing of a pair of long, possibly complex, bars under tight manufacturing tolerances where small variations in manufacturing will cause the loss of mobility or might require introduction of play and subsequent loss of accuracy.

Another system that departs from the double-parallelogram approach as introduced by U.S. Pat. No. 5,397,323 is described in WO 2004/037103. Whereas U.S. Pat. No. 5,397,323 employs two sliding links and means to make both links move at equal amounts in order to create the translational degree of freedom DOF3, WO 2004/037103 introduces a method that employs as much as four sliding links to establish two planar degrees of freedom DOF2, DOF3. Also, this approach is based upon the double parallelogram mechanism, whereby the first parallelogram at the base is being shortened and stretched in the longitudinal direction parallel to the instrument axis.

WO 2004/037103 foresees in two sets of double parallelogram mechanisms that operate in parallel planes. The individual parallelograms are connected via horizontal connection bars and jointly move when actuated. Four slides are thus needed to shorten and stretch the pair of first parallelograms closest to the base. The lower parallelograms are organised in two pairs of two links that pivot and slide at a constant offset around two parallel axes. The angle between sides of the parallelogram which corresponds to DOF2 is controlled by a motor parallel to the pivot axis and transmitted via belt mechanism. Through the various connection bars between the parallelograms this motion is transmitted to the different sliding bars and finally towards the instrument. WO 2004/037103 foresees in a pair of rack and pinions to provide translational degree of freedom DOF3.

A belt is used to synchronise the motion of the pair of pinions. Again, imperfect synchronisation leads to loss of the RCM. As described above, relying on high pre-tensioned belts is not reliable as correct synchronisation cannot be guaranteed and large amounts of friction are introduced. In such case costly high-precision zero-play timing belt, pinions and high-precision zero-play rack and pinions need to be employed. All components must be stiff to ensure correct synchronisation under varying load. As a result the entire assembly becomes heavy and quickly cumbersome in assembly.

Similar to U.S. Pat. No. 5,397,323, the method by WO 2004/037103 requires instrument axis and driving axes to be parallel. Limitations on workspace, limited flexibility in designing dynamics, manipulability, gravity compensation means identified in U.S. Pat. No. 5,397,323 are also present in WO 2004/037103.

Also, the transmission from the local to the remote site of the mechanism further relies on four parallel bars that move relatively with respect to each other, this complicates the design of a compact end-effector that needs to accommodate for these four connecting bars.

To progress MIS practice it would be desirable to devise and implement mechanical solutions that are not or to much less amount hampered by abovementioned drawbacks. In particular, the systems described above with remotely actuated translational degree of freedom DOF3 do possess a large range in the mechanism's roll angle of rotation DOF1, but only allow a limited working range in the pitch rotation angle DOF2 and require additional means to overcome straight angles where parallelograms might otherwise shift into isosceles trapezoid resulting in a loss of the RCM.

SUMMARY OF THE INVENTION

It is an object of the present invention to provide an alternative and possibly improved device and method for minimal invasive surgery comprising a remote center of motion.

It is another object of the present invention to provide a robotic apparatus for minimal invasive surgery comprising a remote center of motion.

Therefore, according to aspects of the invention, there is provided an apparatus as set out in the appended claims. Advantageous aspects are set out in the dependent claims.

According to aspects of the invention, an apparatus for generating motion around a remote center of motion comprises a distal link, a proximal link and a base link. The distal link is arranged to revolve about the remote center of motion, i.e. to revolve about an axis of rotation comprising the remote center of motion. The distal link is also arranged to translate through the remote center of motion, which corresponds to a translation along radial directions of the axis of rotation of the distal link on the remote center of motion, i.e. directions perpendicular to and intersecting the axis of rotation at the remote center of motion.

The proximal link is arranged to revolve about a proximal center of motion through a rotational joint and a sliding joint. This is to effect rotation of the proximal link about the proximal center of motion, i.e. a rotation about an axis of rotation comprising the proximal center of motion, and to effect translation relative to (or through) the proximal center of motion, i.e. a translation along directions coinciding or parallel to radial directions of the axis of rotation of the proximal link on the proximal center of motion, i.e. directions perpendicular to the axis of rotation of the proximal link and possibly intersecting the axis of rotation, advantageously at the proximal center of motion. The above rotation and translation of the proximal link occur in a plane of motion of the proximal link which is perpendicular to the axis of rotation of the proximal link about the proximal center of motion.

The axes of rotation of the distal link on the remote center of motion and of the proximal link on the proximal center of motion are advantageously parallel. The base link is adapted to be coupled to a mounting fixture. The proximal center of motion is coupled to the base link.

The apparatus further comprises a first mechanism. The first mechanism comprises a first link pivotally coupled to the proximal link and to the distal link. The pivotal coupling between the first link and the proximal link defines an intermediate point in constant relative relation to the first link. The intermediate point advantageously lies on a pivot axis between the first link and the proximal link and advantageously corresponds to a pivot point between the proximal link and the first link. The pivotal coupling between the first link and the distal link defines a remote point in constant relative relation to the first link. The remote point advantageously lies on a pivot axis between the first link and the distal link and advantageously corresponds to a pivot point between the distal link and the first link. The pivot axes between the first link and the proximal link and between the first link and the distal link are advantageously parallel to the axis of rotation of the proximal link (about the proximal center of motion). The first mechanism is operable to transfer motion of the proximal link relative to the proximal center of motion to a motion of the distal link relative to the remote center of motion by maintaining a parallelogram between orthogonal projections of the proximal center of motion, the distal center of motion, the intermediate point, and the remote point on the plane of motion of the proximal link. Advantageously, the parallelogram is maintained between the proximal center of motion, the distal center of motion, the intermediate point, and the remote point. Advantageously, the parallelogram is perpendicular to the axis of rotation of the proximal link (about the proximal center of motion). A length between the intermediate point and the proximal center of motion is adjustable due to the ability of the proximal link to translate through the proximal center of motion.

The apparatus further comprises a second mechanism having at least two degrees of freedom. The second mechanism is coupled to the first link and is operable to move the first link according to two degrees of freedom in a plane perpendicular to the axis of rotation of the proximal link (about the proximal center of motion) and such that orthogonal projections of the first link and of an axis extending from the proximal center of motion to the remote center of motion on the plane of motion of the proximal link are parallel.

According to aspects of the invention, the second mechanism comprises at least one link (i.e. a single link or a serial connection of links) connecting the base link to the first link, wherein each one of the at least one link arranged in the linkage chain connecting the base link to the first link has an orientation of instant motion relative to the base link which is different from the orientation of instant motion of the proximal link, and advantageously different from the orientation of instant motion of the first link as well. Advantageously, the apparatus does not comprise any link or serial connection of links connecting the base link to the first link, which have a same orientation of instant motion relative to the base link as the proximal link, when one disregards the distal link.

It will be convenient to note that the instant motion of the at least one link (i.e. of the single link connecting the base link to the first link, or of each link of the serial connection of links connecting the base link to the first link) can be a (linear) translation, a rotation or a combination of both. In case of a (linear) translation, the different orientation of instant motion refers to the fact that the at least one link moves along a direction relative to the base link which is different (i.e. not parallel) compared to the direction of motion of the proximal link relative to the base link. In case of a rotation, the different orientation of instant motion refers to the fact that the at least one link instantly assumes an orientation relative to the base link which is different (i.e. not parallel) compared to the orientation of the proximal link relative to the base link, such that the instant direction of rotary motion is not parallel. It is however possible that in a limited number of discrete positions of the proximal link, the directions of motion or the orientation of the at least one link and the proximal link are instantly parallel, but change as soon as the position or orientation of the proximal link is changed.

For determining an orientation of a link, an axis extending between two pivot points of the link can be considered.

Either one or both of the first and the second mechanism is advantageously planar, i.e. is advantageously a planar motion mechanism.

Advantageously, the at least one link of the second mechanism is configured to be actuated for moving the first link, whereas the first mechanism is passive. Alternatively, the proximal link can be configured to be actuated so as to move the first link and the distal link, whereas the second mechanism is passive. A combination of the above actuation schemes in order to obtain redundancy is possible.

Aspects of the invention offer one or a combination of the following advantages.

In one or more aspects, apparatuses of the invention offer improved stability of the RCM point and instrument positioning in up to 4 DOFs w.r.t. this RCM by virtue of a mechanical mechanism that is extremely compact at its end-effector. The stability of the RCM point is superior to alternative systems that are designed to occupy few space at the end-effector, such as U.S. Pat. No. 5,397,323 and WO 2004/037103, and that require two or more sliding bars that need to maintain parallelism and need to extend and retract in equal amounts for correct working, imposing functional tolerance constraints on all connecting linkages and pivots, whereas tolerance constraints related to the single sliding bar and connecting linkages of the embodiments associated to the current invention are non-functional and thus impose less tight manufacturing requirements. Alternative systems need to be constructed with prohibitively high manufacturing tolerances to achieve a stability nearing that of the present invention and that loose mobility otherwise or require admission of a non-negligible amount of play to lower the required manufacturing tolerances and loose RCM point stability at that point.

The space occupancy at the end-effector is far less than typical RCM mechanisms and can be made less than that of alternative systems that are designed to occupy few space at the end-effector, as the present invention only requires a single connection bar to drive the parallelogram that is connected to the end-effector, whereby alternative systems need at least two driving bars to drive the parallelogram at the end-effector side. The extremely low space occupancy gives surgeon maximal maneuverability and minimal hindered access to the surgical site, but also simplifies the combined use of multiple devices that can work jointly at incision points that are closer to each other than possible with alternative systems.

The achievable position and manipulation precision is superior to that of alternative systems that are designed to occupy limited space at the end-effector, where too tight manufacturing constraints would render the mechanism prohibitively expensive and relaxation of such constraints requires addition of play for the mechanisms to work which on their turn limit the achievable position and manipulation precision. This makes the invention more adequate and safer in use for amongst others micro-surgical interventions where high precision is a key requirement.

In one or more aspects, apparatuses of the invention comprise compact and highly configurable mechanisms at the end-effector providing an unprecedented range of freedom to optimally design and adjust an RCM mechanism to a targeted surgical procedure and sets of targeted surgical procedures. The unprecedented range of design freedom originates from the single parallelogram at the end-effector being connected by only a single connection bar to the corresponding two- or three-degree-of-freedom driving mechanism and as such provides more freedom to reposition the single parallelogram with respect to the driving mechanism and as such affect practically all possible design parameters including but not limited to the overall mechanism's workspace, dynamics, gravity compensation means and so on. All alternative compact RCM mechanisms require at least two connection points between the final parallelogram and the driving mechanism and as such do not have the same design freedom. For example all methods based on double parallelogram mechanisms with distally actuated translational degree of freedom DOF3 require the instrument to be mounted parallel to the corresponding links of the sets of the driving parallelograms. This makes it more difficult to achieve very obtuse and acute pitch angles as at that point the different links of the parallelograms might collide, also there is fewer freedom in designing balancing means, manipulability or general dynamic behaviour of the mechanism as by design all abovementioned links are parallel.

The RCM and the mechanism's workspace can be adjusted conveniently by adapting the length of a single linkage (connection between driving mechanism and the single parallelogram at the end-effector), where alternative RCM mechanisms propose to adjust at least two linkages to affect the position of the RCM with respect to the mechanism's base. Complex, bulky and carefully manufactured synchronisation mechanisms that are needed to synchronise the pairwise displacements can be avoided as such. Note, that the possibility to adjust the location of the RCM by adjusting a pair of linkages as is the case in alternative systems is also possible with the current invention.

The RCM and the mechanism's workspace can be adjusted conveniently by adjusting the position of a single pivot point (namely the LCM), where alternative RCM mechanisms require adjustment of at least two pivot points to affect the position of the RCM with respect to the mechanism's base. All embodiments associated with the present invention allow design, offline or online adjustment of the RCM and associated workspace related to the pitch angle of the instrument by simply displacing or reorganising the location of the LCM along the axis connecting LCM with RCM. This can be used beneficially to reach very obtuse or acute angles without requiring the driving mechanism to maintain similar obtuse or acute angles as would be the case in alternative systems. Furthermore, a set of embodiments allow design, offline or online adjustment of the RCM and associated workspace in as much as 3 degrees-of-freedom by simply displacing the LCM in 3 degrees-of-freedom with respect to the mechanism's base, whereas for alternative systems achieving the 3 degree-of-freedom RCM adaptation by adjusting of the mechanism itself is completely impractical requiring a complex mechanism, complex coordination and control of a multitude of linkages and joints.

In one or more aspects, apparatuses of the invention provide a safe, reliable, practical and intuitive mechanism. Several means for safety and reliability can be foreseen, but one particularly appealing safety feature that is not available in other RCM mechanisms is the possibility to embed redundancy in sensing and actuation and estimate and control the instrument's pose by two independent sensing/actuation mechanisms working on two independent kinematic chains between base link and the instrument. As a matter of fact both the driving mechanism as well as the mechanisms at the level of the LCM can be equipped with independent sensors and actuators. The instrument pose can therefore be steered by actuating the driving mechanism, but it could equally well be steered by actuating the set of joints at the level of the LCM. In latter case the function of the—at this point not anymore—driving mechanism is simply to keep the single parallelogram at the end-effector parallel to the axis connecting LCM to RCM. Also knowledge of the pose of bar LI w.r.t the base link provides full knowledge of the instrument's 4 DOF just as the knowledge of the pose of the driving mechanism does. It is thus fairly easy to prepare two separate independent sensing, actuating and braking mechanisms, a feature which is not present in alternative RCM systems.

In one or more aspects, apparatuses are particularly safe and convenient to be designed for use in a sterile and electrically insulated environment nearby the patient. This is true especially when compared to typical RCM mechanisms, but also when compared to alternative RCM mechanisms that foresee a proximal actuation of the distal translational motion. Just like latter alternative RCM mechanisms and compared to traditional RCM mechanisms, it is easy to ensure patient safety against electric shock by nearby motors or burns induced by the heat generated by nearby motors as motors are placed further away from the patient and electrical insulation can be more easily inserted somewhere between both. Additionally, compared to all types of RCM mechanisms it is easier to design means to maintain a sterile operation field. The design of a sterile connection piece at the level of the instrument is challenging given space constraints. Also, the use of surgical drapes that close to the patient which cover the remainder of the mechanical structure is quite impractical. Surgical drapes that close by might block the view. Such drapes can easily lead to obstruction, especially when using multiple instruments and/or robots and they can lead to serious sterilisation problems in case of rupture. For RCM mechanisms with distal actuation of the translation degree of freedom it is possible to foresee an alternative connection place upon a shielding sterile drape, namely by dividing the parallelogram into two pieces. One side can then be draped; the other side can be made from sterilisable or disposable material. While this option is also available in the proposed embodiments a more convenient approach would be to foresee a connection at the single bar connecting the driving mechanism and the parallelogram at the instrument's side and another connecting at LI. Latter solution would pose no particular demands on manufacturing tolerances of these connection pieces, whereas the first solution requires very careful production and connection of both sides of the parallelogram. Inaccurate manufacturing, inadequate connection or variation in shape of the connection bars due to deformation, wear or the like could lead to an instable RCM point, immobilise the mechanism, cause unnecessarily high friction or play affecting the achievable positioning accuracy.

In one or more aspects, apparatuses of the present invention allow proximal actuation of up to 4DOF instrument motions with respect to the RCM, and intuitive, full and simultaneous access to the surgeon to co-manipulate all the 4 motion degrees-of-freedom by a single handle that is conveniently placed for the surgeon. In a preferred embodiment described in this document an intermediate location close-by but not hindering the workspace near the incision point, namely as an extension of an axis collinear to LI. The $4^{th}$ DOF (DOF 4) is conveniently transferred to LR by means of a cardan pair with connecting timing belt attached to the single handle at one side and the instrument at the other side. A similarly intuitive and purely mechanical one-to-one mapping of the motion of a single bar (handle) of the mechanism to the instrument motion has not been described in earlier work.

In one or more aspects, apparatuses of the present invention are easier to manufacture and control compared to other RCM mechanisms with distal actuation of the translational degree of freedom DOF3, requiring, thanks to the single sliding bar, mainly non-functional manufacturing tolerances and allowing embodiments where the translational degree of freedom DOF3 can be controlled by means of a combination only consisting out of rotary actuators mounted in direct drive to a concatenation of rigid linkages of the driving machine; thus avoiding the use of expensive or friction inducing zero-play rack and pinions or similar; not needing either the use of cable-based transmissions that could be installed to modify by means of a driving pulley rotary motion from a rotary actuator to a translational motion of sliding bar, but introduce compliance and load-depending displacement causing loss of accuracy or RCM stability; not needing the use of linear actuators to be mounted along the axis of the sliding bars either as such linear actuators would need to rotate along and add as such extra inertia to the pitch motion DOF and as such linear actuators are in general more costly and show lower performance than rotary actuators of a similar price class.

Compared to the prior art, in one or more aspects, apparatuses of the present invention can be made cheaper and easier to control as not needing to compensate for additional flexibility or play. Such system can be exploited ideally to remove surgical tremor and increase motion precision by programming various levels of damping, but can be equally designed to further reduce the mental workload of the surgeon and to provide additional safety measures by e.g. partial automation of the procedure or through introduction of shared control strategies.

In an aspect, apparatuses are described for generating motion around a remote center of motion, comprising at least one of the following components:

a distal link (referred to as member) arranged to revolve about the remote center of motion and to translate through the remote center of motion;

a base link adapted to be coupled to a mounting fixture;

a first mechanism (referred to as a planar parallel mechanism, i.e. a mechanism ensuring planar parallel motion) comprising a first link and a second link whereby said first and second link are parallel to each other along a first direction which is parallel to the base link and whereby said planar parallel mechanism is adapted to position the member in two degrees-of-freedom in the plane of said planar parallel mechanism; and a two degree-of-freedom joint adapted to be attached to the base link, whereby said two degree-of-freedom joint is adapted to move a proximal link with two degrees-of-freedom in a plane parallel to that of the said planar parallel mechanism, whereby said two degree-of-freedom joint is adapted to allow the proximal link to slide in and out through the two degree-of-freedom joint and to allow the proximal link to revolve about the axis of the degree-of-freedom of the two degree-of-freedom joint that is perpendicular to the said planar parallel mechanism;

whereby said proximal link and member remain parallel to each other along a second direction, and whereby said first and second link position said member such that it rotates and slides through the remote center of motion.

Preferably, the remote center of motion is located at a fixed position with respect to the two degree-of-freedom joint. More specifically, the fixed position is preferably determined by the dimensions of the second link. In preferred embodiments the first, second, member and proximal link form a parallelogram. Preferably, the base link is pivotally coupled to the mounting structure.

Preferably, the apparatus further can comprise means to rotate the planar parallel mechanism and the two degree-of-freedom joint about an axis (A0) that connects the origin of the two degree-of-freedom joint and the RCM resulting in a three degree-of-freedom RCM, whereby as origin of the two degree-of-freedom is considered the intersection of the revolution axis of the two degree-of-freedom joint perpendicular to the said planar mechanism and the plane of the said planar mechanism. Preferably, the means to rotate is a cradle.

In preferred embodiments, the apparatus is servo mechanical.

Preferably, the two-degree-of-motion of the first link in the first planar mechanism is transmitted mechanically via a second preferably planar mechanism that connects the actuators at the base link to the first link, whereby the second mechanism ensures the parallelism between the first link and the base link. In other preferred embodiments the two-degree-of-motion of the first link in the first planar mechanism is transmitted via a two-degree-of-motion actuator that is integrated in the said two-degree-of-motion joint and whereby, a second mechanism connects the base link to the first link, ensuring the parallelism between the first link and the base link.

In alternative embodiments the two-degree-of-motion of the first link in the first planar mechanism is transmitted via any combination of actuators driving the two-degree-ofmotion joint and a second mechanism that connects the base link to the first link that ensures the parallelism between the first link and the base link.

Preferably the second mechanism can comprise a combination of at least nine linkages including the base link and the first link that together form a set of three parallelograms, whereby each parallelogram is connected to each other via one link they have in common.

In preferred embodiments, any combination of parallelograms pertaining to the first planar mechanism and/or the second planar mechanism can be replaced by a flexible drive.

In other preferred embodiments the second (planar) mechanism comprises, or consists of, a pair of non-parallel links or linkages, arranged obliquely between the links or linkages and advantageously wherein links within each linkage are oblique (non-parallel) as well, such that the extremities of each side of the pair of links or linkages are parallel, whereby the linkages are moved by a pair of linear actuators or combinations of rotary actuators with appropriate transmission systems that generate a linear motion such as e.g. based on combinations of pulleys and cables.

In other preferred embodiments the second planar mechanism consists of a pair of orthogonally placed linkages, whereby the linkages are moved by a pair of linear actuators or combinations of rotary actuators with appropriate transmission systems that generate a linear motion such as e.g. based on combinations of pulleys and cables. Preferably the second planar mechanism can comprise a three-DOF mechanism with three actuators, whereby the parallelism between base link and the first link is achieved by appropriate coordinated control of the three actuators.

Preferably the proximal link that rotates and slides inside the two degree-of-freedom joint and is always parallel to the said member, is dimensioned of appropriate size and equipped with a mechanical interface that serves as a handle, that can be grasped by the operator to steer the robot in cooperated manipulation modus.

In preferred embodiments one or several mechanical interfaces that serve as handles, that can be grasped by the operator to steer the robot in cooperated manipulation modus, may be mounted at different convenient locations on the mechanism to steer one, two or three degrees-of-freedom of the robot in cooperated manipulation modus and whereby any moving linkage of the mechanism can be identified as a so-called convenient location, provided it is convenient for the targeted use of the mechanism.

In preferred embodiments a pressure, contact, proximity, force or torque sensor may be positioned in the handle that can be used to measure the pressure, contact, proximity, forces or torques exerted by the operator and used in various control schemes to improve the quality and safety of the operation, for example, but not limited to, control schemes that filter out tremor by the user, that compensate for undesired friction, damping or inertia inside the mechanism, that avoid impacts when reaching joint limits or limitations on the range of the mechanism, that activate brakes when contact or grip is lost, that consist of virtually programmed boundaries or haptic guidance schemes.

Preferably the member link may be carrying an actuation mechanism to rotate a link about an axis parallel with this member link that passes the 3 degree-of-freedom mechanism, so that the mechanism generates a total of 4 motion degrees-of-freedom.

Preferably the first link or the second link may be carrying an actuation mechanism to rotate a link about an axis parallel with the member link and a means to transmit the motion of the actuator to the motion of the second link, so that the instrument has a total of 4 motion degrees-of-freedom.

In embodiments of the present invention the apparatus further may comprise means to rotate a fifth linkage about an axis collinear to the axis of the proximal linkage, and a means such as, but not limited to, a double cardan mechanisms attached to both the fifth linkage and the end-effector and connected by a belt, is foreseen to transfer this rotational motion to the end-effector of the mechanism, in such way effectively generating a 4 degree-of-freedom RCM mechanism. Preferably the fifth linkage rotates in a plane parallel to the plane of the planar mechanism and at the same time slides in and out through the two degree-of-freedom joint, while remaining in the plane parallel to the planar mechanism. More preferably, the apparatus can be foreseen by one or more handles adapted to be operated in co-manipulation modus, also known as hands-on modus.

In other embodiments the apparatus further may comprise a remote center of motion linkage mechanism, to transfer a local two degrees-of-freedom to a remote point and adding a rotational degree of freedom around the base of the mechanism.

In preferred embodiments the links of the parallelograms are designed so that their internal contacts form 'natural' and mechanical boundaries on the desired reachable workspace.

In other preferred embodiments the position of the two degree-of-freedom joint can be adjusted manually or motor-controlled so as to program the location of the RCM with respect to the base of the mechanism and so as to adjust the workspace of the mechanism.

In preferred embodiments the link lengths of the first link and the second link can be adjusted in same amounts manual or motor controlled, so as to program the location of the RCM with respect to the base of the mechanism and so as to displace the workspace of the mechanism.

In other preferred embodiments the apparatus may further comprise general elements that are adjustable in length so as to allow reconfiguration of the mechanism and adjustment of the linkage structure to mechanically program the workspace.

In preferred embodiments the apparatus may be mounted upon a second system that can position the mechanism in up to maximally 6 degrees-of-freedom in space so as to determine the position of the RCM and to locate the manipulator's workspace, aligning it in an appropriate manner with respect to the desirable working range in the patient body or so as to determine the position of the RCM and to modify the manipulator's occupancy so that it does not collide with other manipulators, medical instruments, staff or patient.

According to other aspects of the invention, there are provided methods of operating apparatuses of the invention as set out in the appended claims.

In aspects, such methods can comprise autonomously positioning a RCM and the orientation of the workspace, by controlling the second mechanism in an up to 6 degrees-of-freedom in space.

Methods can autonomously position the RCM and the orientation of the workspace and comprise controlling the second mechanism in an up to 6 degrees-of-freedom in space, by using sensory data from external sensor data.

Possibly, the second mechanism is controlled in an up to 6 degrees-of-freedom in space, by using sensory data from external sensors from which an estimate is being made of the location on the human body where the instrument is to enter that human body, such as the location of a trocar or entry port.

Methods can autonomously position the RCM and the orientation of the workspace, comprising controlling the second system in an up to 6 degrees-of-freedom in space, by using sensory data from external sensors from which in a continuous fashion an estimate is being made of the location on the human body where the instrument is to enter that human body, such as the location of a trocar or entry port.

Methods can autonomously position the RCM and the orientation of the workspace, comprising controlling the second system in an up to 6 degrees-of-freedom in space, by using sensory data from internal sensors such as for example force-sensitive sensors from which in a continuous fashion an estimate is being made of the location on the human body where the instrument is to enter that human body, such as the location of a trocar or entry port.

BRIEF DESCRIPTION OF THE DRAWINGS

The invention may be better understood, and further advantages and uses thereof more readily apparent, when considered in view of FIG. 1 displaying the targeted 4 remote DOFs available during a general MIS procedure and in view of the following detailed description, taken with the accompanying drawings, which represent as follows.

FIGS. 2A-2C are schematic drawings showing different views of the kinematic principle of a mechanism generating 3 remote degrees of freedom of which the proposed inventions pose particularly interesting embodiments. FIG. 2A shows an isometric view. FIGS. 2B-C show respectively a top view and a frontal view of the mechanism of FIG. 2A.

FIGS. 6A-6C show different views of a scheme showing how the proposed invention can be mounted on top of a positioning stage so that the remote center of motion can be aligned at wish with the entry point into the patient body. FIG. 6A shows an isometric view. FIGS. 6B-C show respectively a top view and a frontal view of the mechanism of FIG. 6A.

Figure 7:
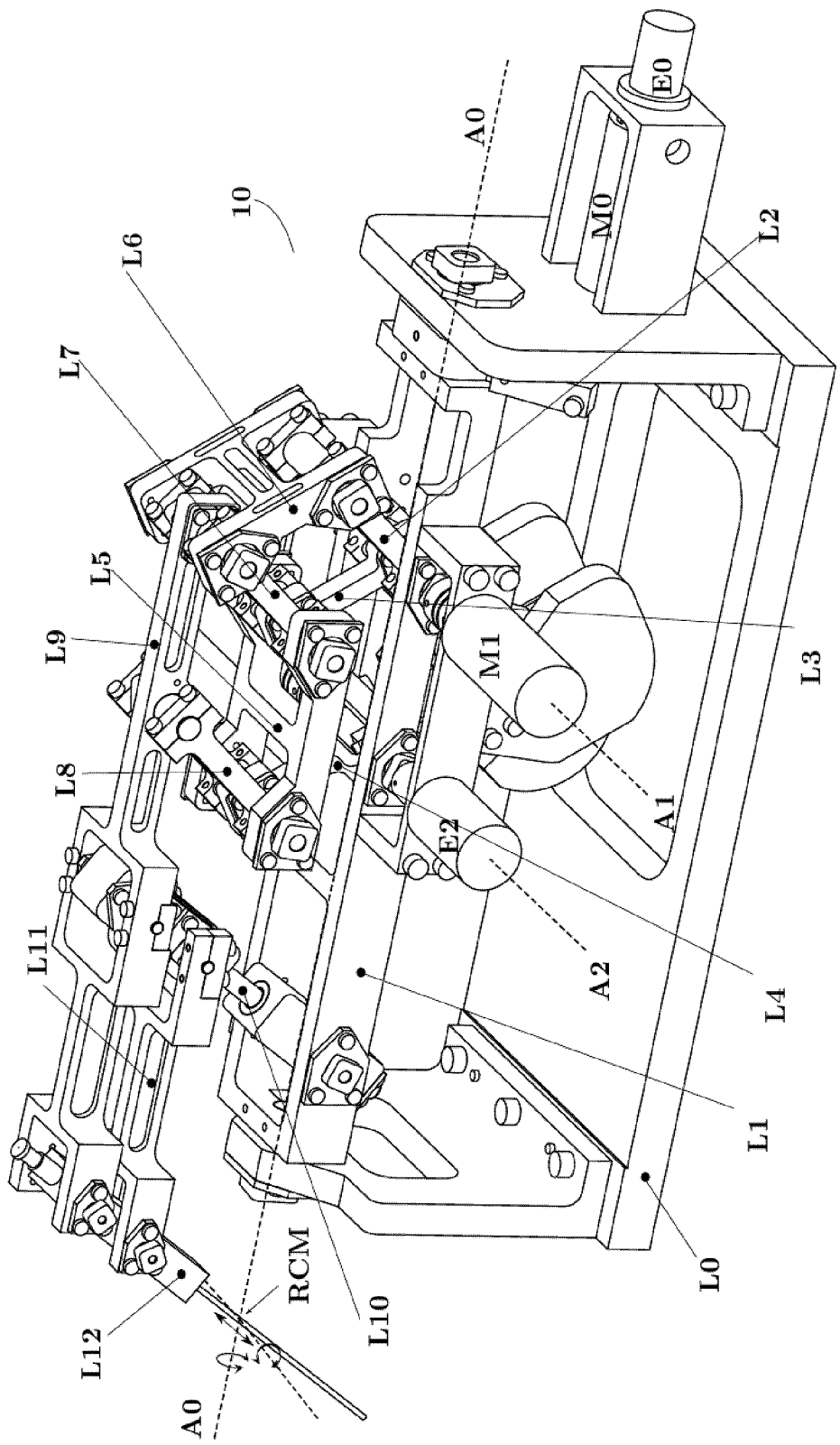
FIG. 7 shows a perspective view on a preferred embodiment of the mechanism seen from the proximal (w.r.t. the surgeon) side of the mechanism.
Figure 8:
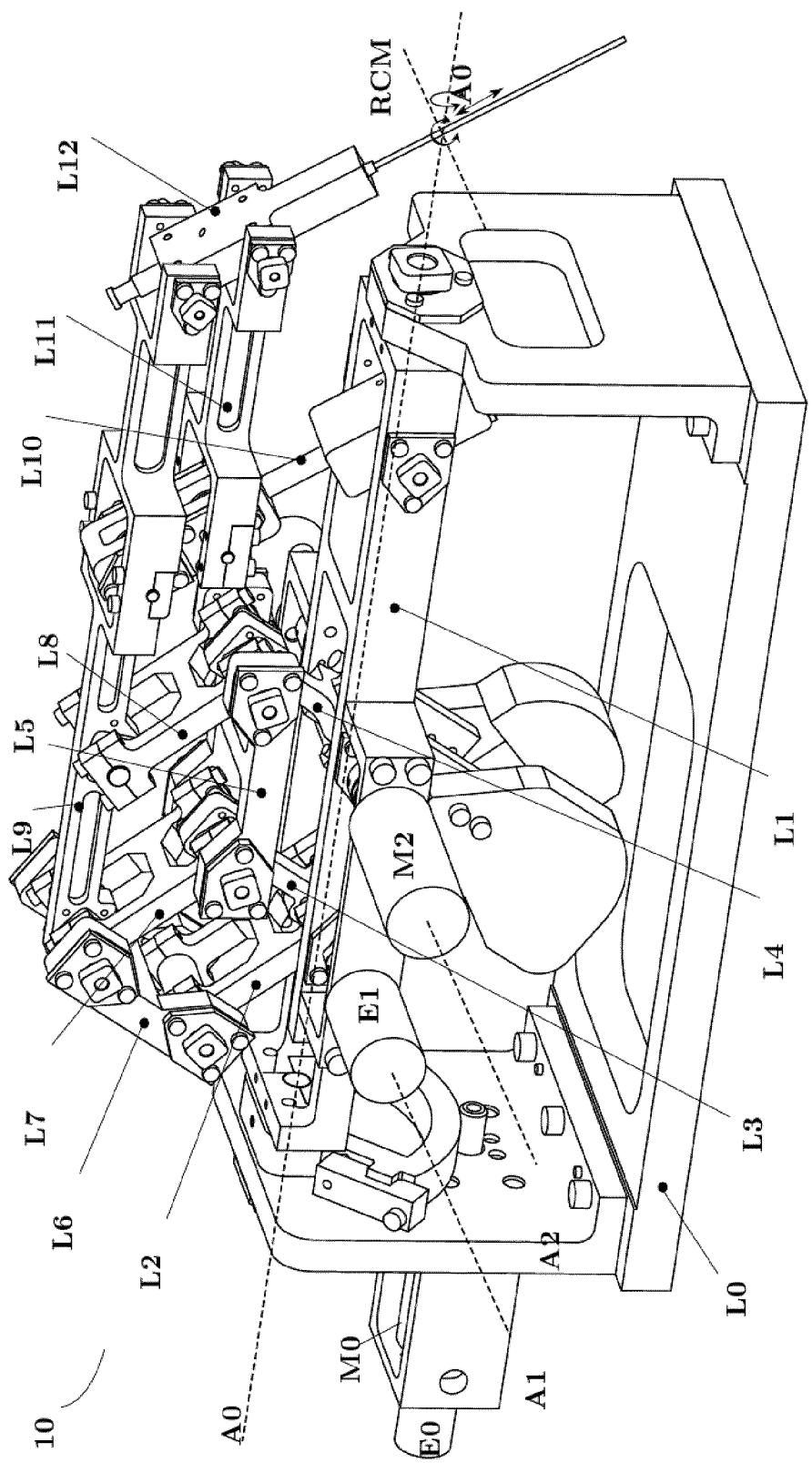
FIG. 8 shows a perspective view on a preferred embodiment of the mechanism seen from the distal side of the mechanism.
Figure 9:
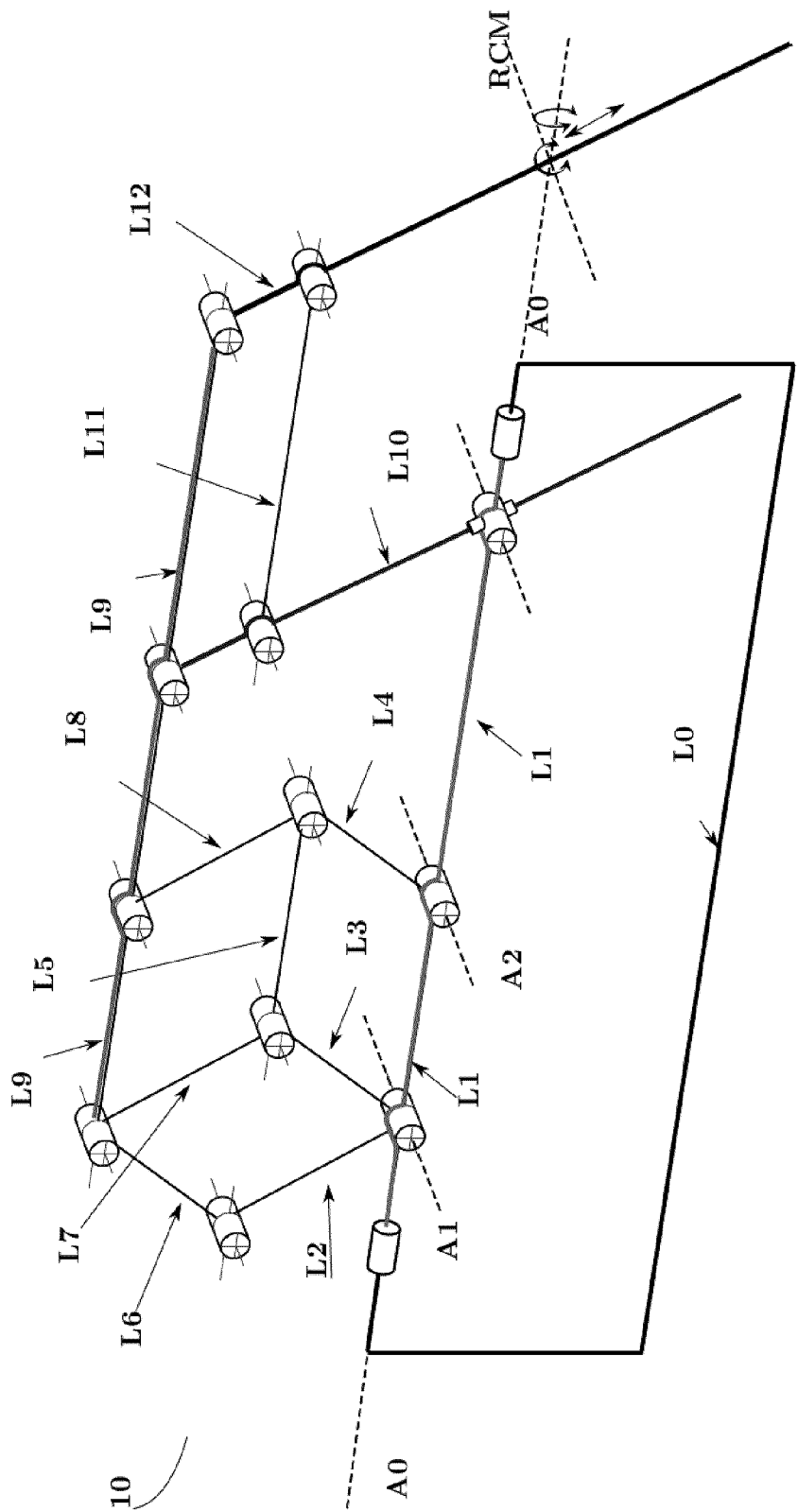

For an improved understanding of the working principle of the preferred embodiment such as it is depicted in FIGS. 7 and 8, a schematic representation of this preferred embodiment is presented in FIG. 9.

Figure 10:
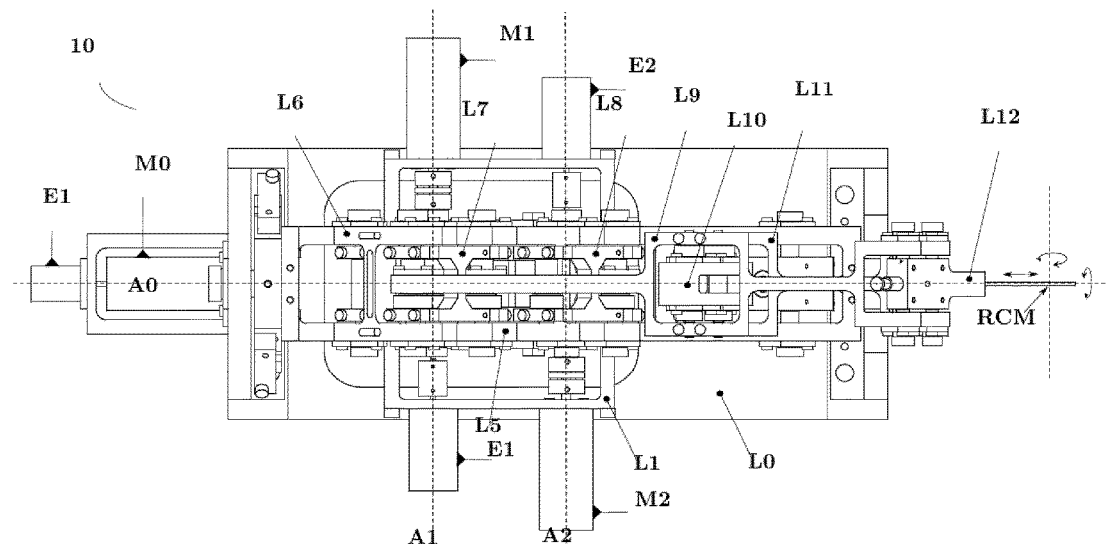

FIG. 10 is a schematic representation in a top view of a preferred embodiment of the invention.

Figure 11:
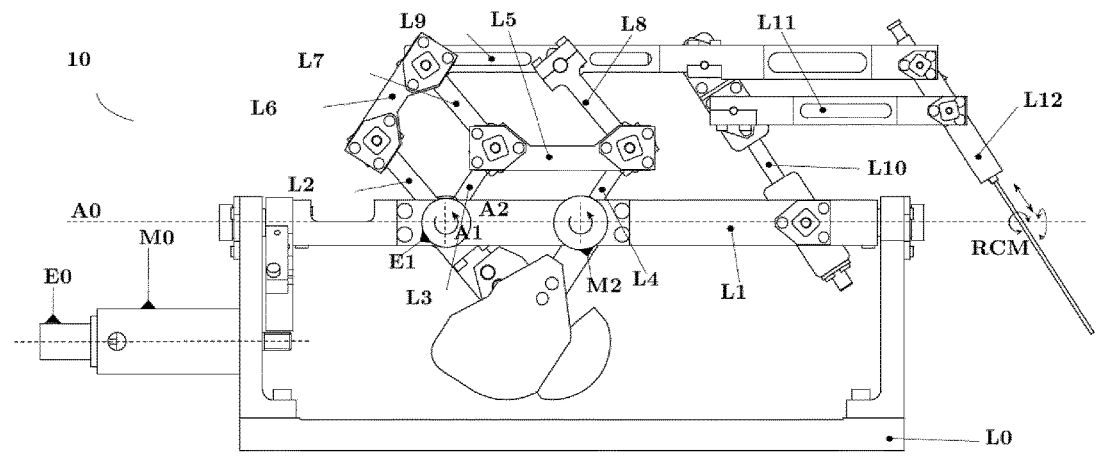

FIG. 11 is a schematic representation in a frontal view of the preferred embodiment.

Figure 12:
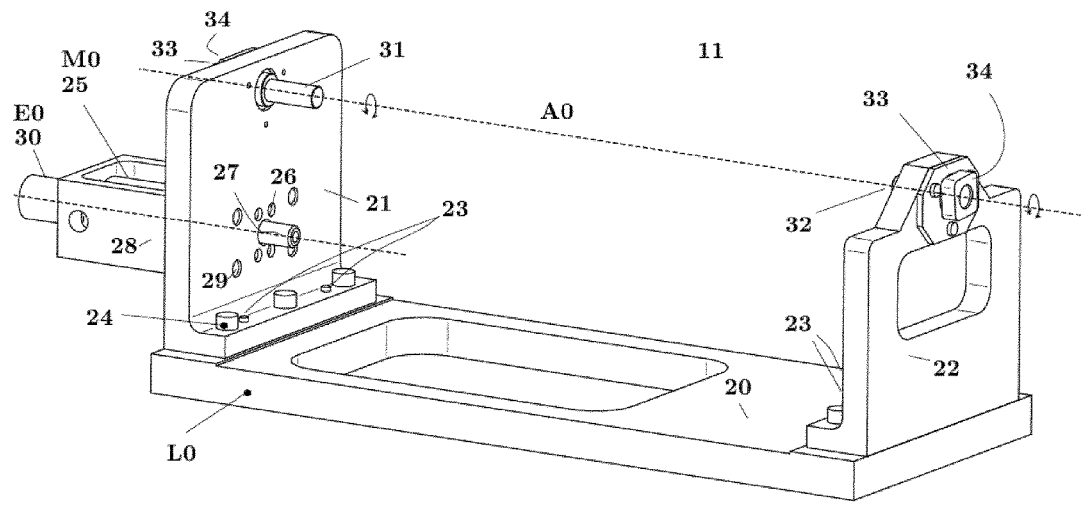

FIG. 12 shows an implementation of the base part of a preferred embodiment of the mechanism.

Figure 13:
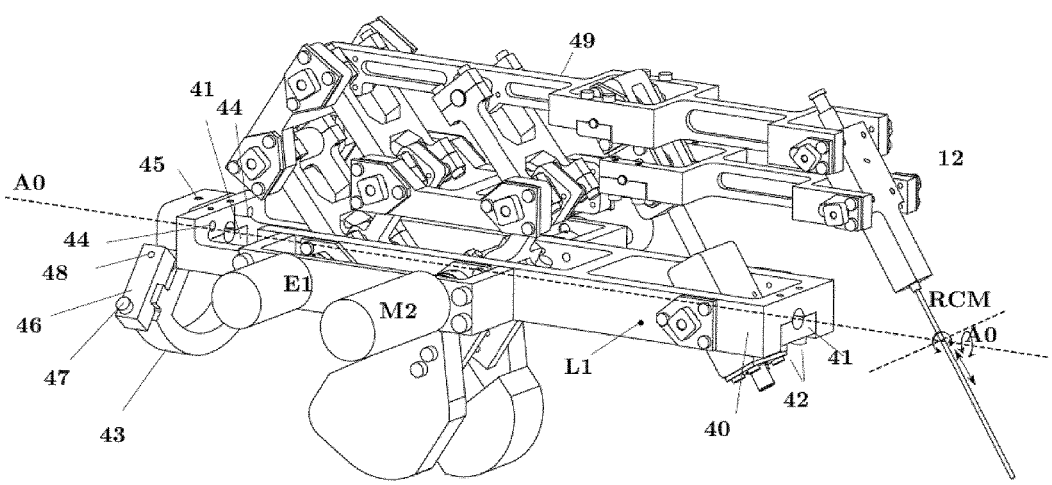

FIG. 13 depicts the cradle part of a preferred embodiment of the mechanism that can be mounted pivotally into the base part of the mechanism that is depicted in FIG. 12.

Figure 14:
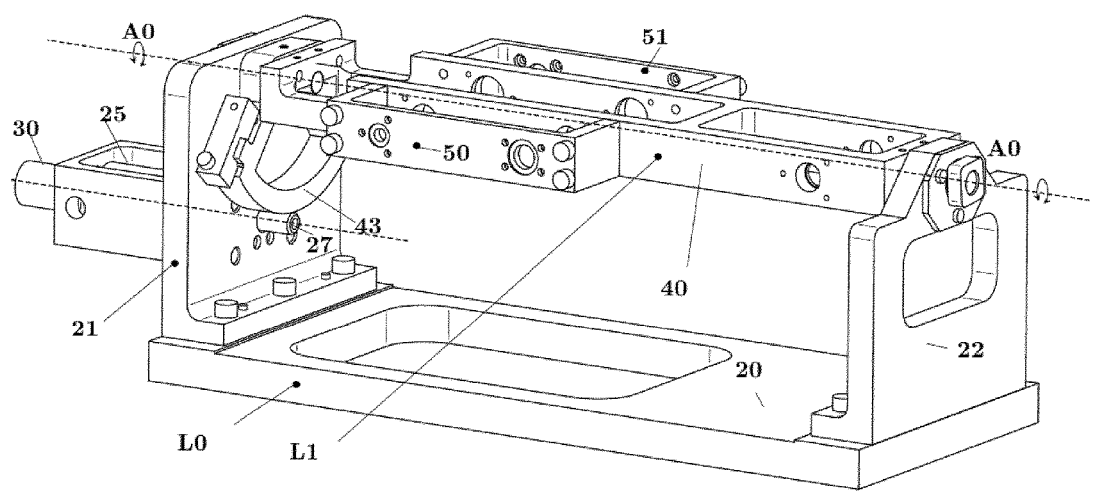

FIG. 14 shows how the frame of the cradle part displayed in FIG. 13 can be mounted pivotally into the base part of FIG. 12 of a preferred embodiment.

Figure 15:
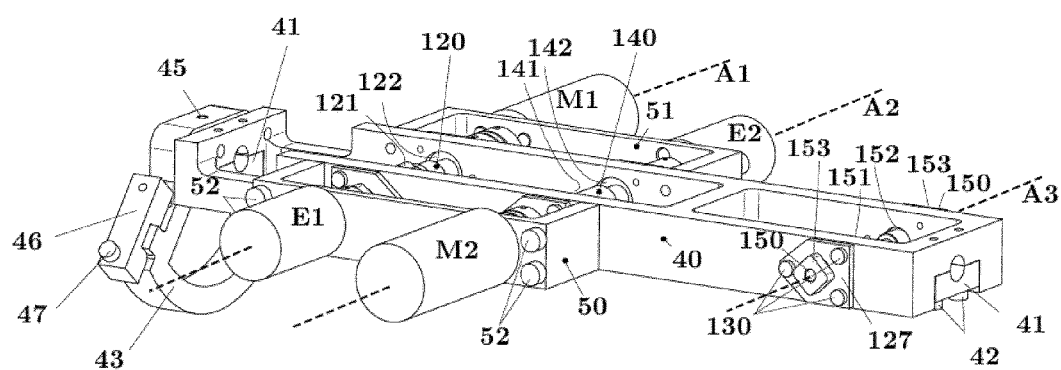

FIG. 15 shows the cradle frame in more detail, with focus on axes A1, A2 and A3 and more in particular displaying the mounting of actuators M1 and M2 and encoders E1 and E2 on A1 and A2 respectively.

Figure 16:
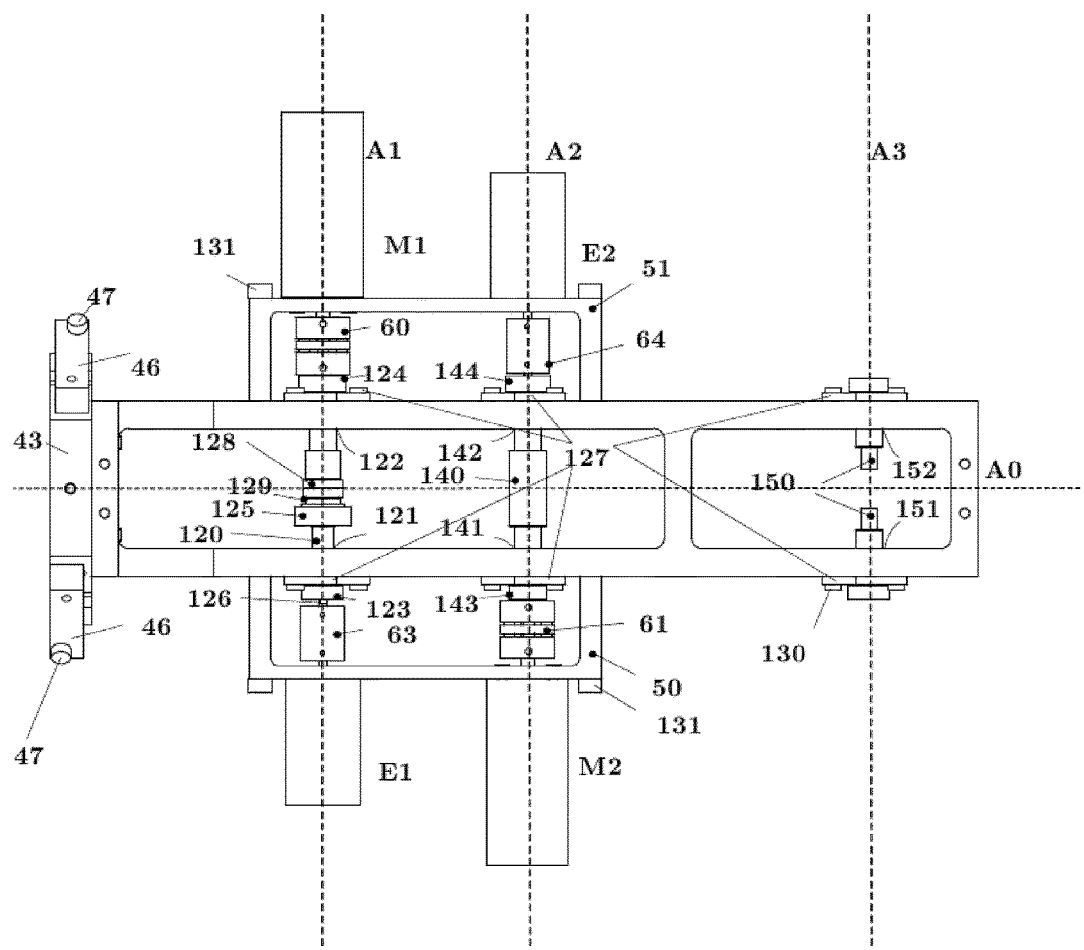

FIG. 16 is a schematic representation in a top view of the cradle frame indicated in FIG. 15.

Figure 17:
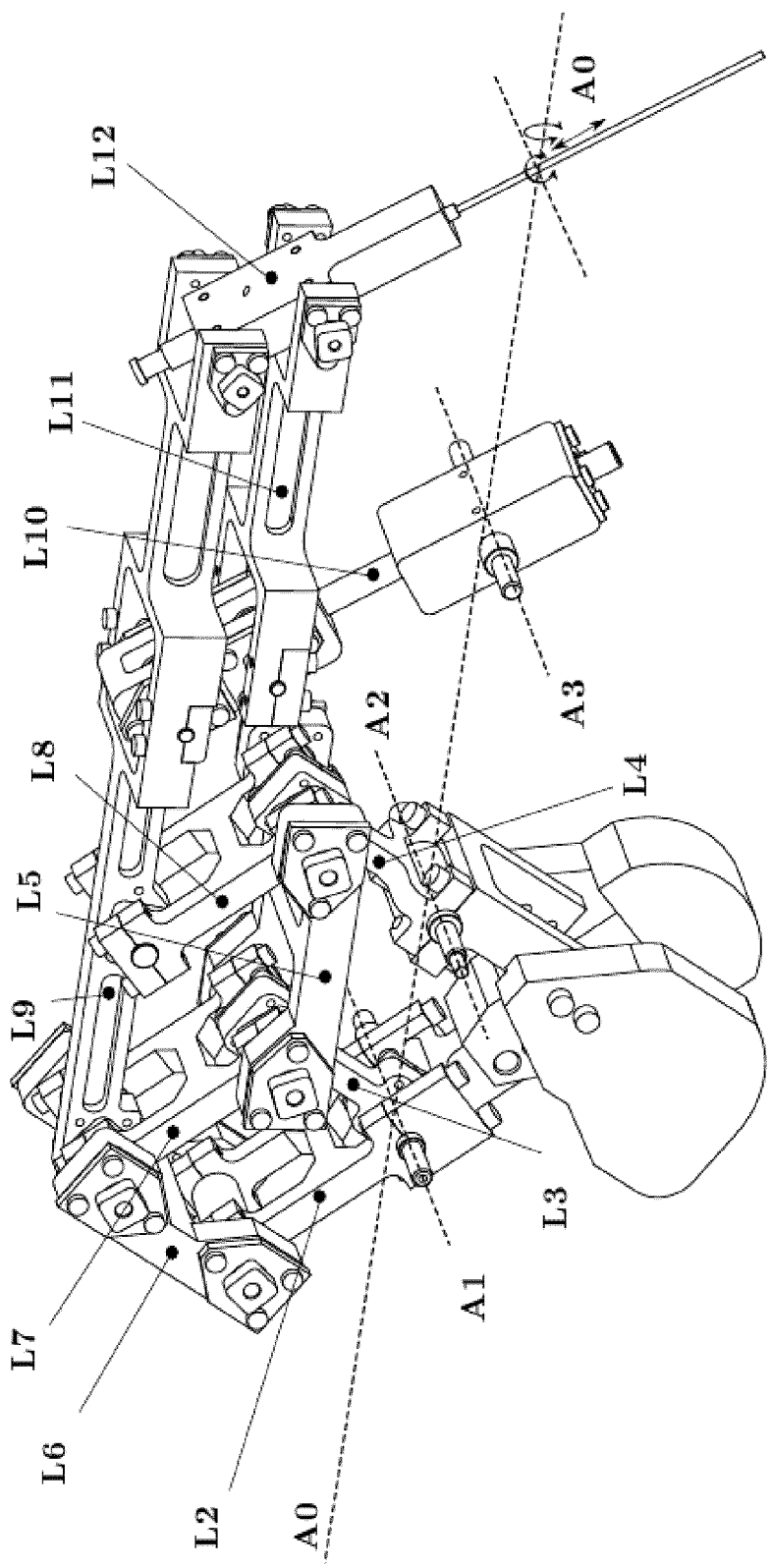

FIG. 17 shows a preferred embodiment of an implementation of the two planar degrees of freedom DOF2, DOF3 that is mounted into the cradle frame of FIG. 14 at A1, A2 and A3, further pivoting in its whole about A0.

Figure 18:
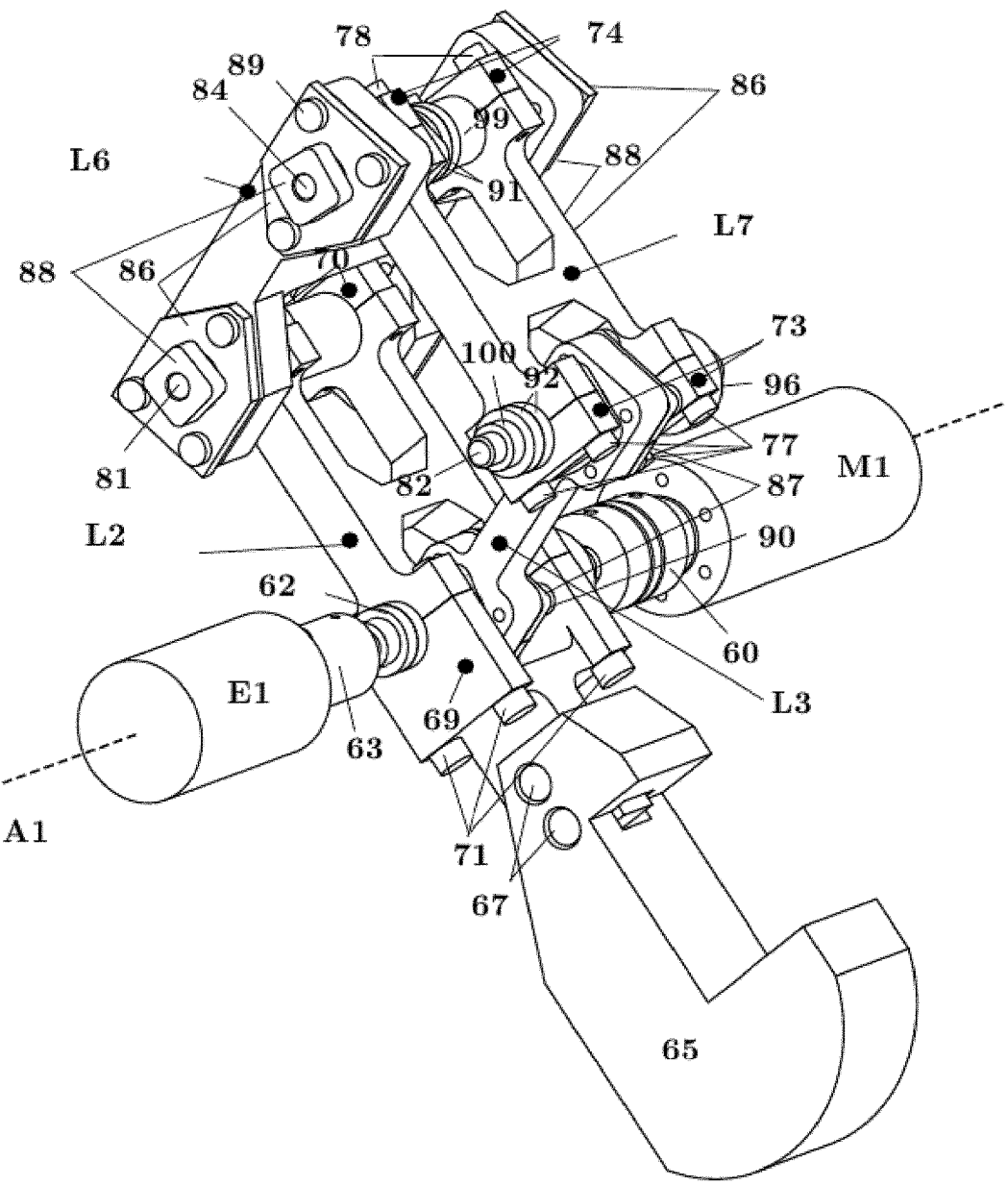

FIG. 18 shows a perspective view on a first parallelogram that forms a part of a preferred embodiment of the two planar degrees of freedom DOF2, DOF3 mechanism of FIG. 17.

Figure 19:
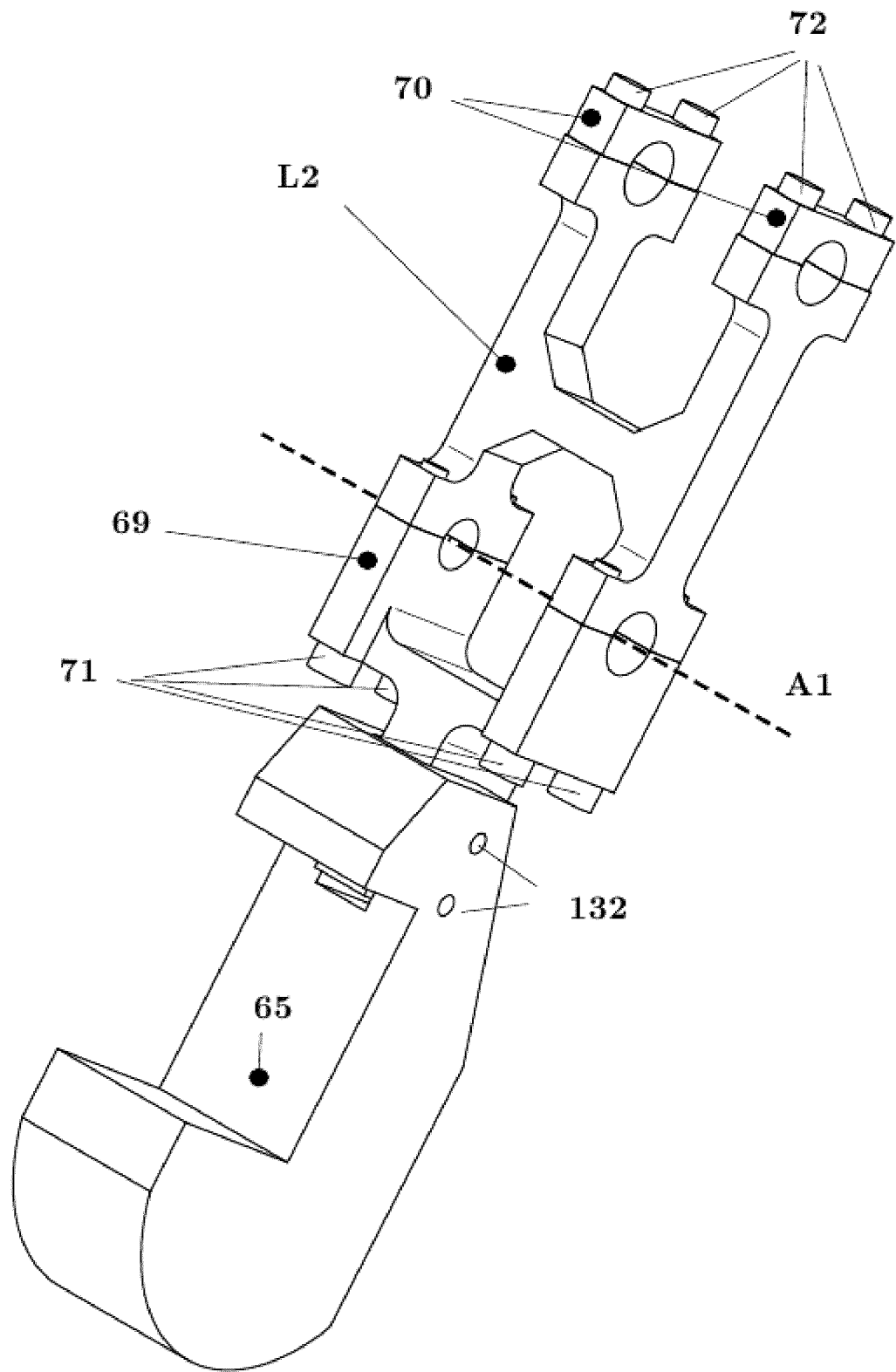

FIG. 19 shows a perspective view on L2 of the said first parallelogram of FIG. 18, clarifying the way it is mounted upon A1 and how the connection with a mechanical counterweight is made in a preferred embodiment.

Figure 20:
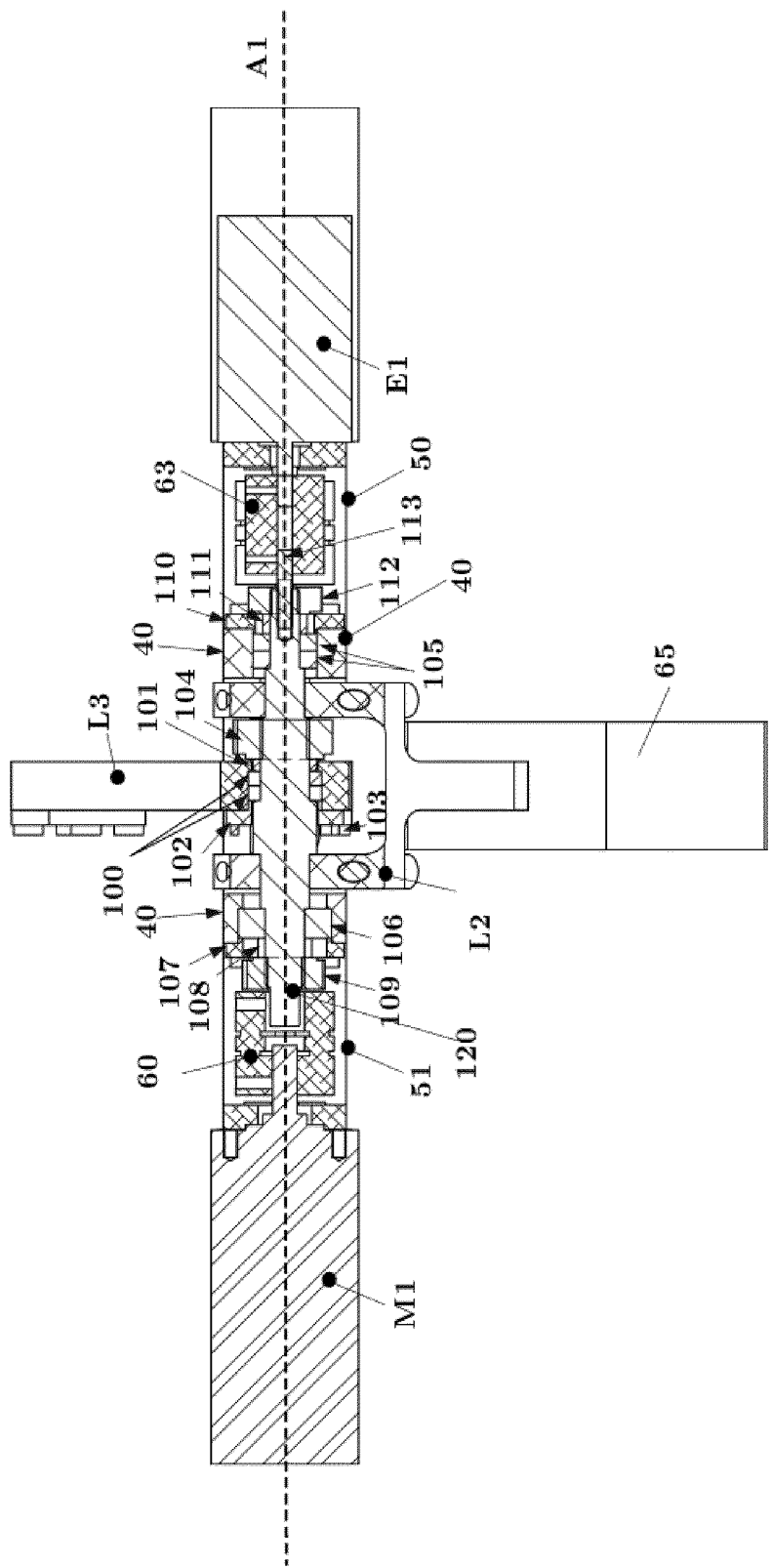

FIG. 20 is a cut through view upon the assembly at A1 indicating a preferred method of mounting L2, L3 and M1 and E1 to A1.

Figure 21:
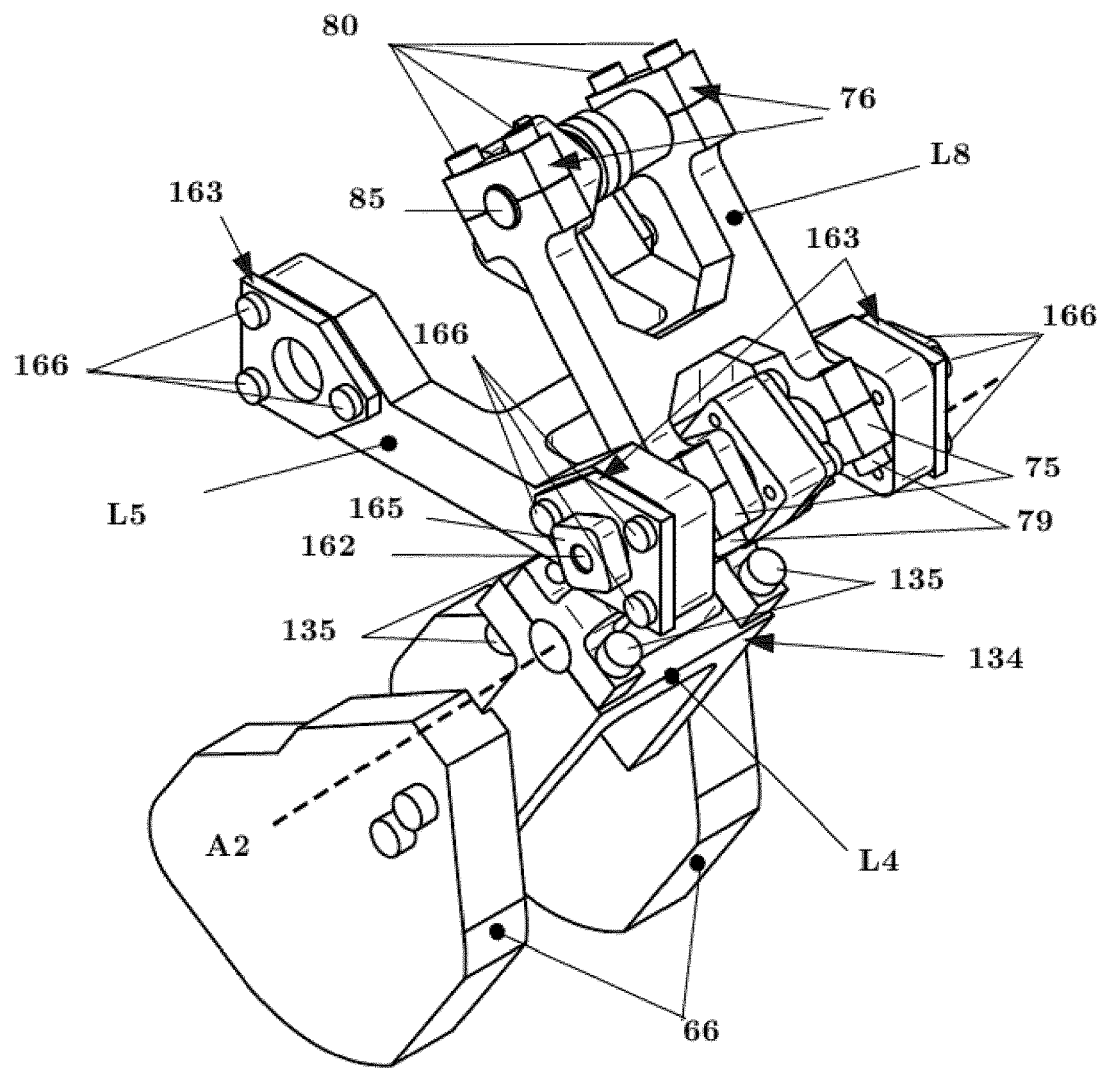

FIG. 21 shows an isometric view on the connection of links L4, L5 and L8 that mounted inside the cradle frame of FIG. 14 at A2 join with the links of the first parallelogram of FIG. 18 to form a first moving base of a preferred embodiment of the two planar degrees of freedom DOF2, DOF3 of FIG. 17.

Figure 22:
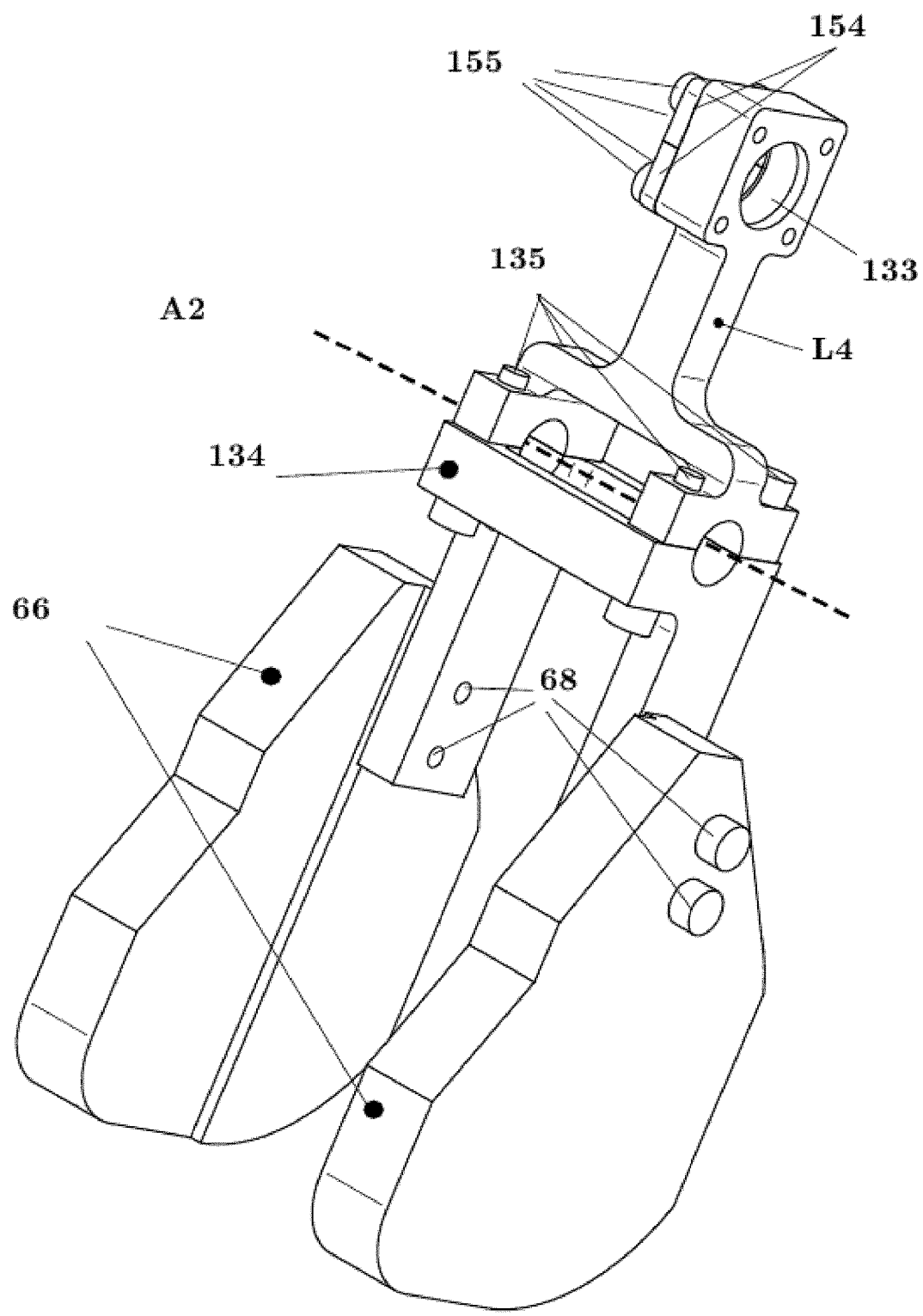

FIG. 22 shows a perspective view on L4, clarifying the way it is mounted upon A2 and how the connection with a pair of mechanical counterweights is made in a preferred embodiment of the invention.

Figure 23:
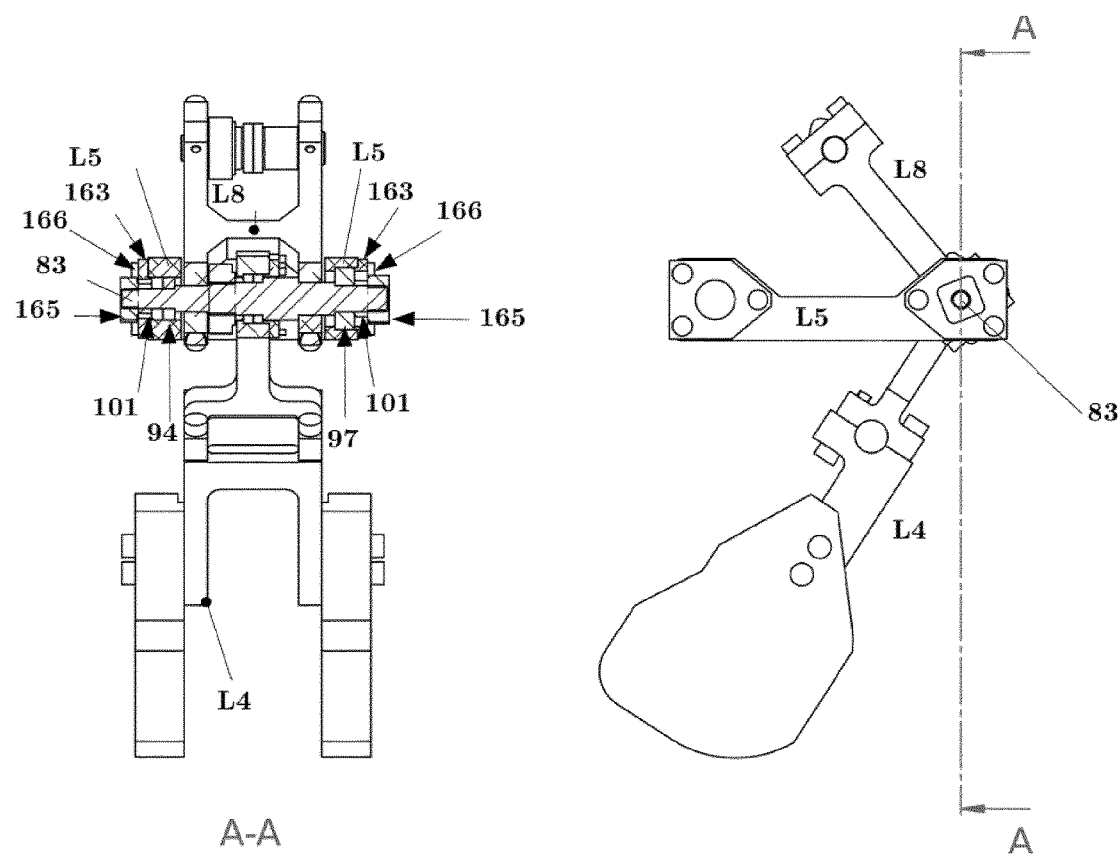

FIG. 23 shows a cross section view of the axis 83 that joins the three links L4, L5 and L8, clarifying the assembly and working of these components.

Figure 24:
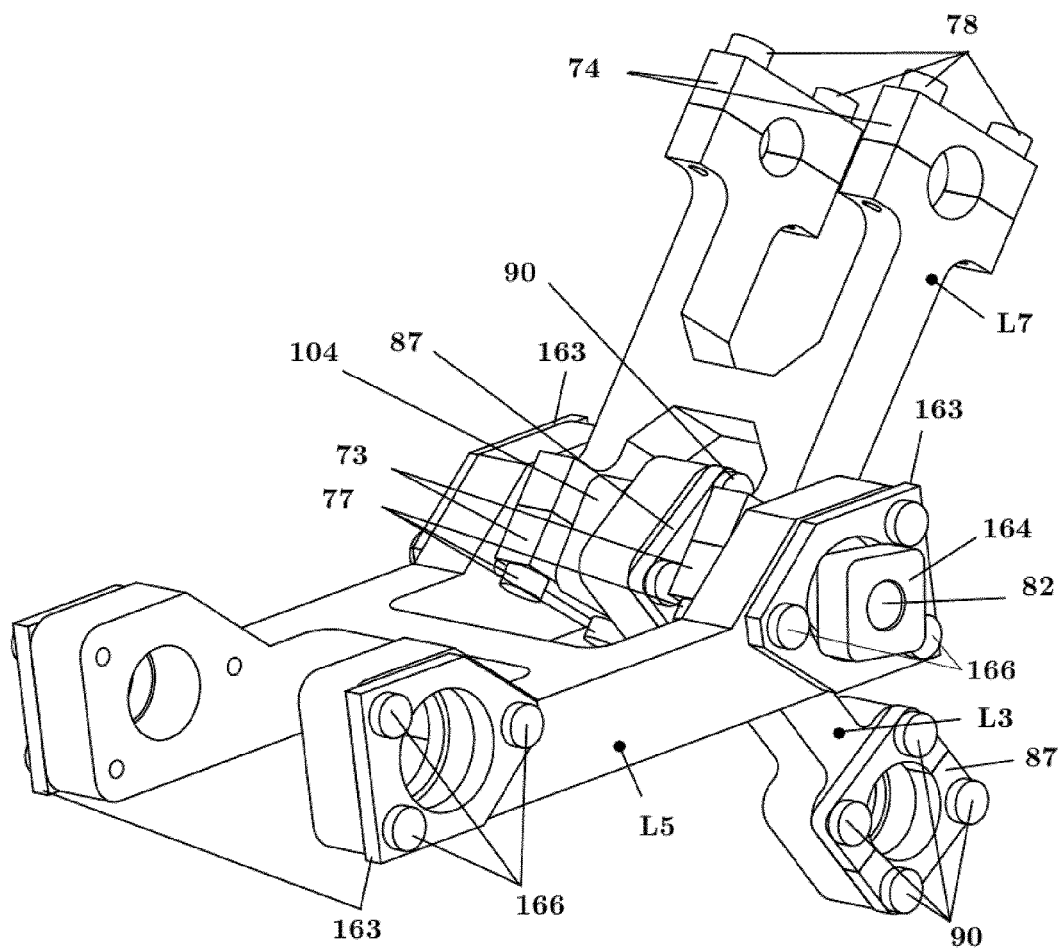

FIG. 24 shows an isometric view on the axis 82 which connects L3, L5 and L7.

Figure 25:
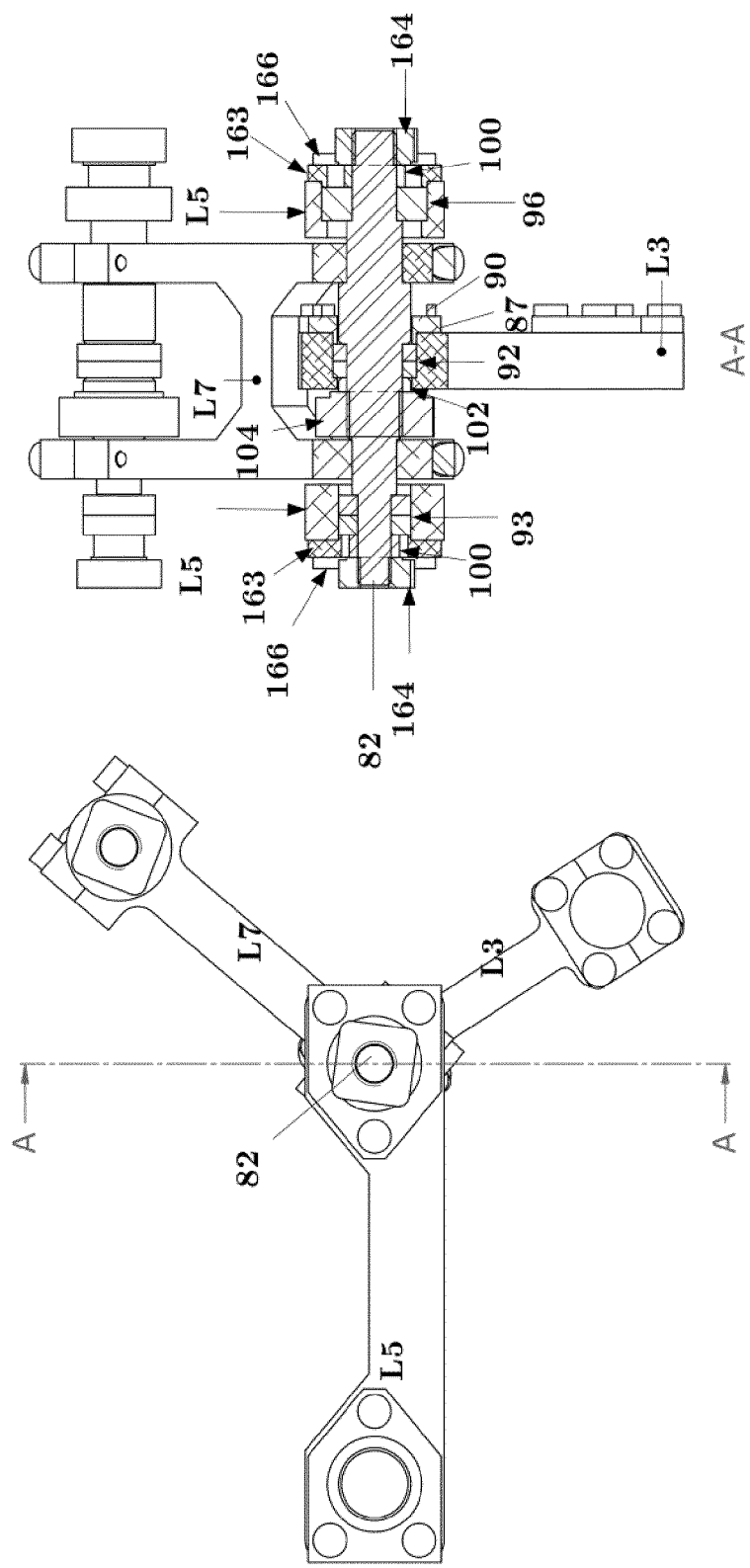

FIG. 25 shows a cross section view of 82 providing further insight on how L3, L5 and L7 are mounted and operating with respect to each other.

Figure 26:
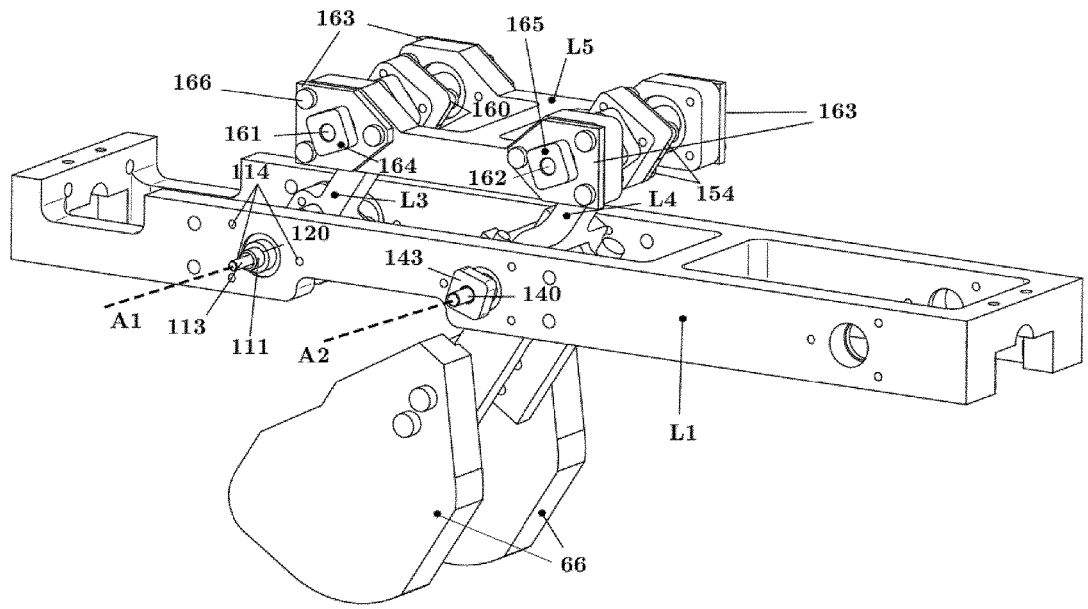

FIG. 26 shows an isometric view of the parallelogram composed out of links L3, L5, L4 and L1 mounted into the cradle frame.

Figure 27:
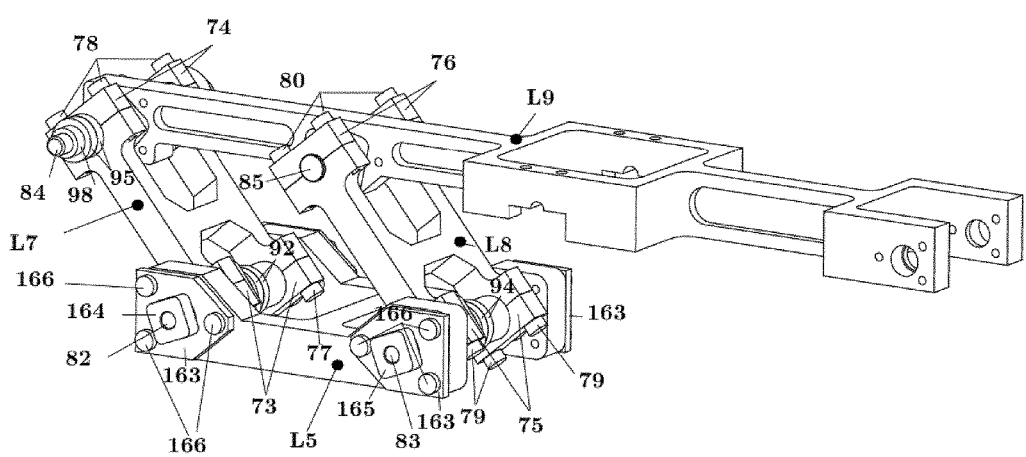

FIG. 27 shows an isometric view of the parallelogram composed out of links L5, L7, L9 and L8. L9 appears here as upper bar extending out of one side of this parallelogram in the direction of the mechanism end-effector.

Figure 28:
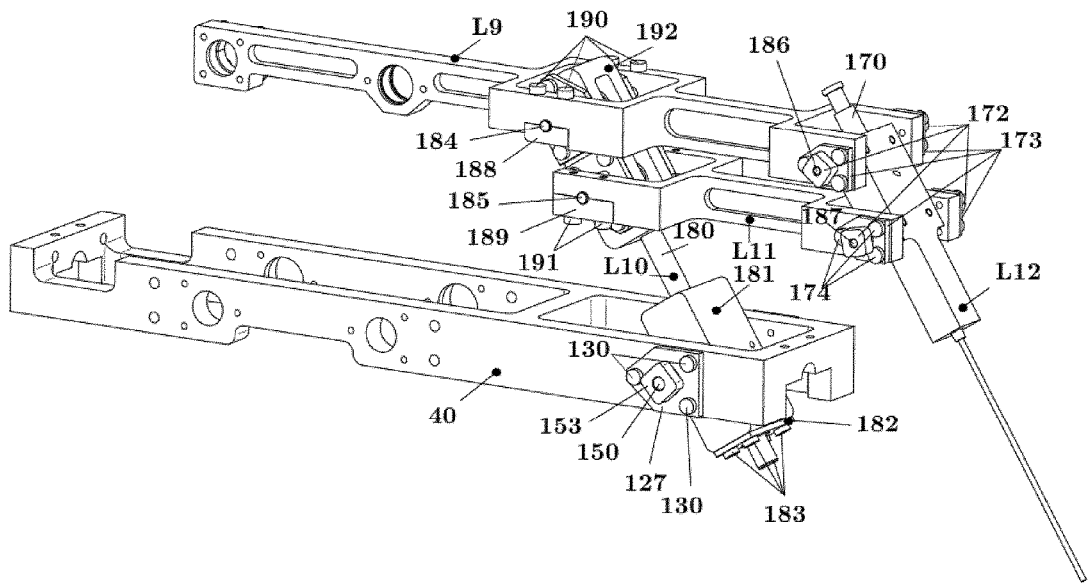

FIG. 28 provides a view upon the frontal parallelogram that transfers the motion around the LCM towards instrument motion around and through the RCM.

Figure 29:
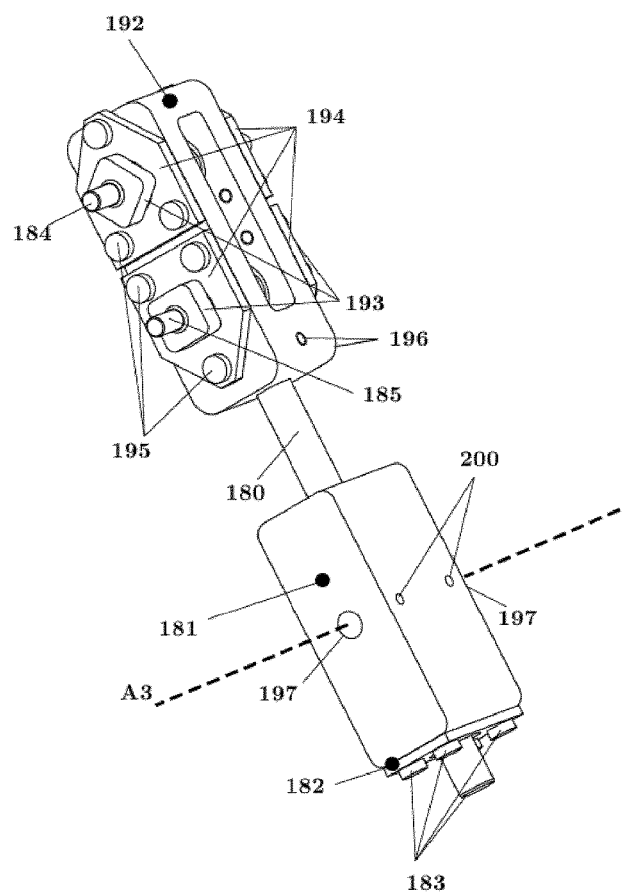

FIG. 29 shows an isometric view upon link L10 inserted into the pivot guide.

Figure 30:
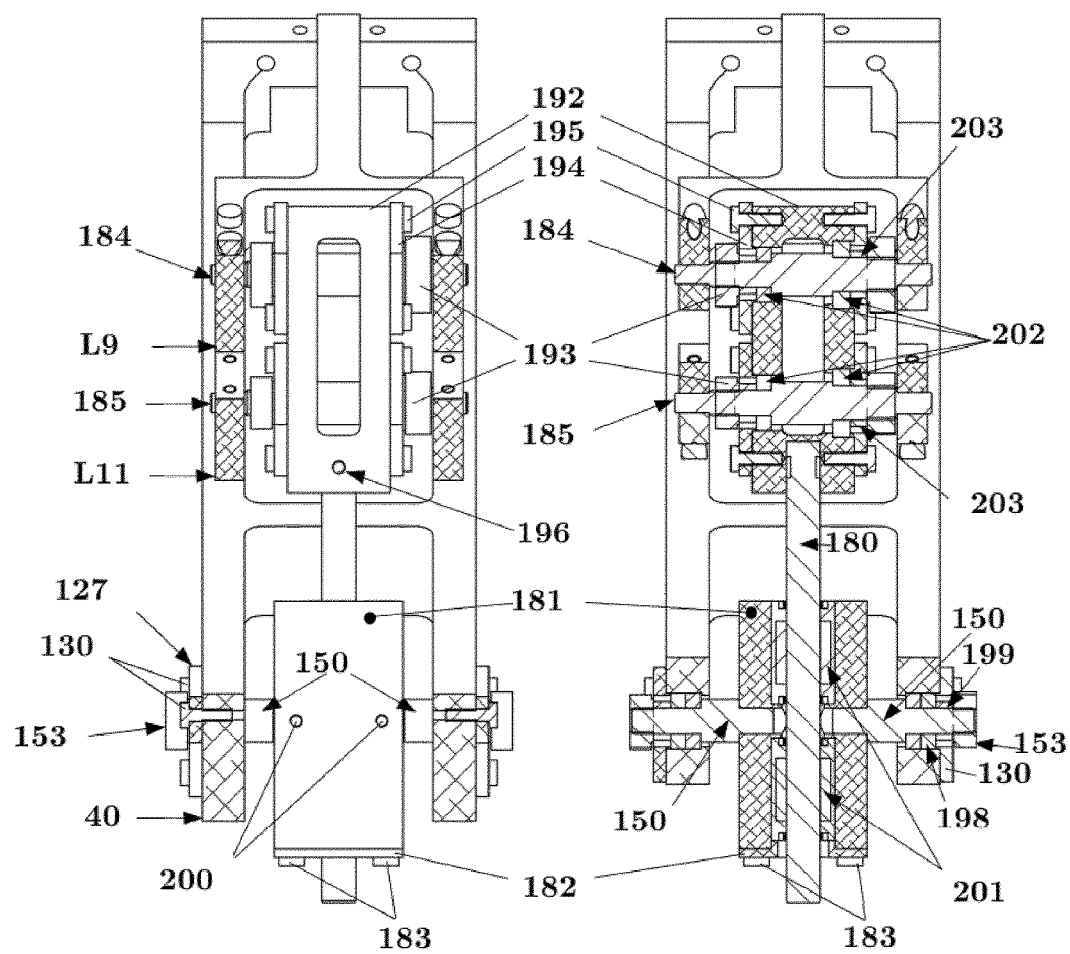

FIG. 30 shows two cross section views upon L10 providing better insight on the assembly of L10 and the layout of the different elements belonging to this link.

Figure 31:
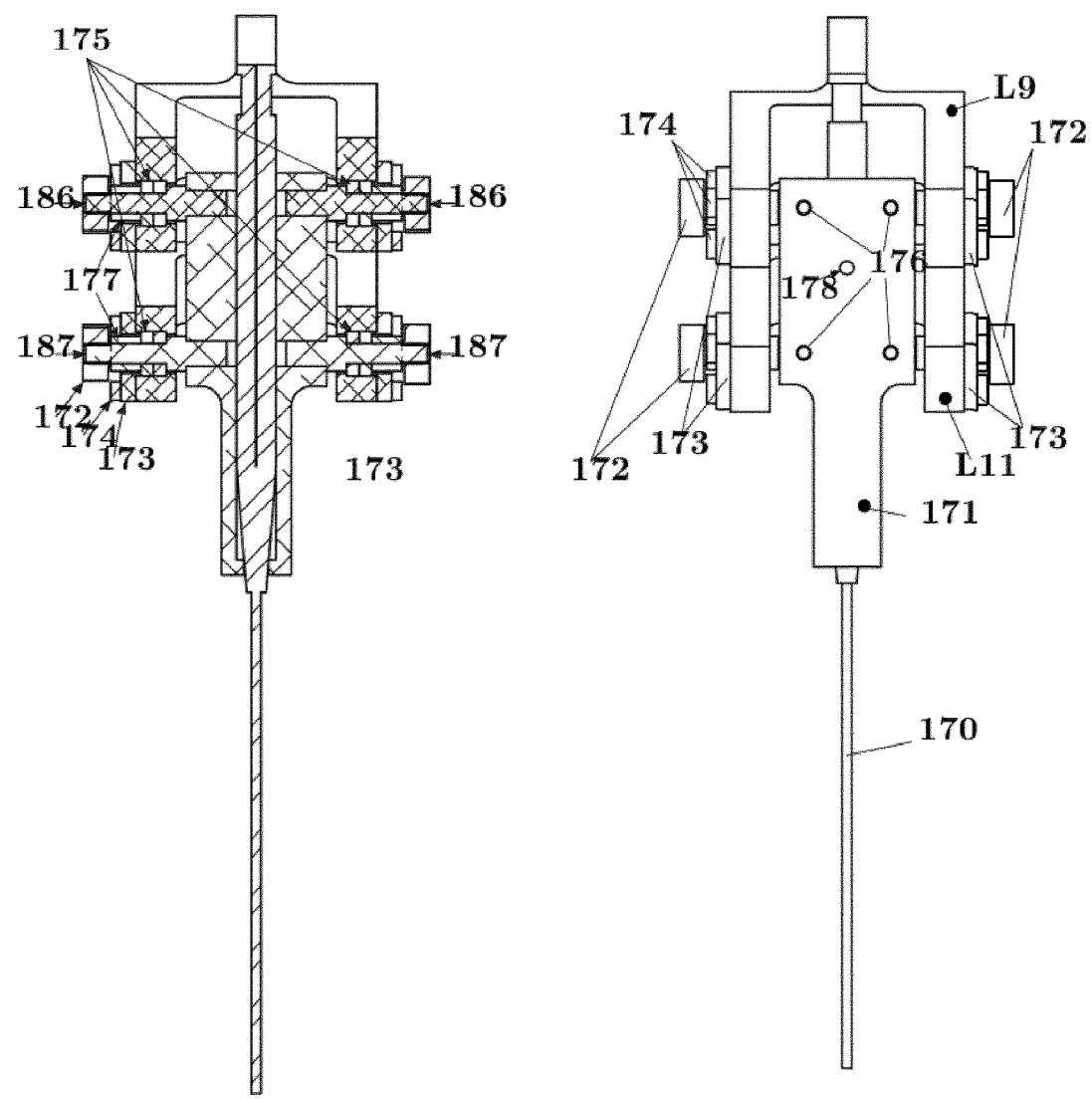

FIG. 31 provides a frontal and cross-sectional view upon a surgical instrument inserted in the instrument holder which is positioned through the pair of links L9 and L11.

Figure 5:
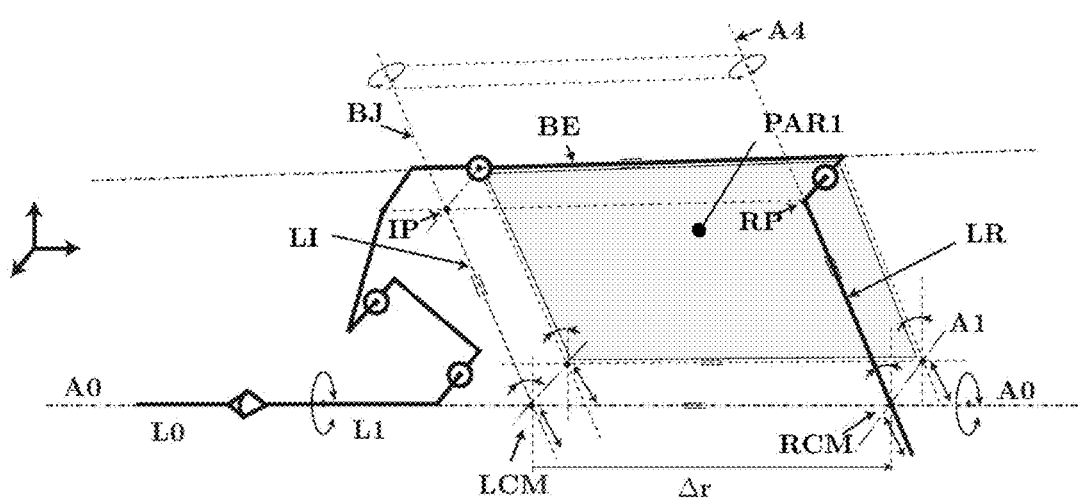
FIG. 5 is a schematic of an extension of the general mechanism depicted in FIG. 2 towards a system that generates 4 remote degrees of freedom all of which can be actuated locally at a safe distance from the end effector.
Figure 32:
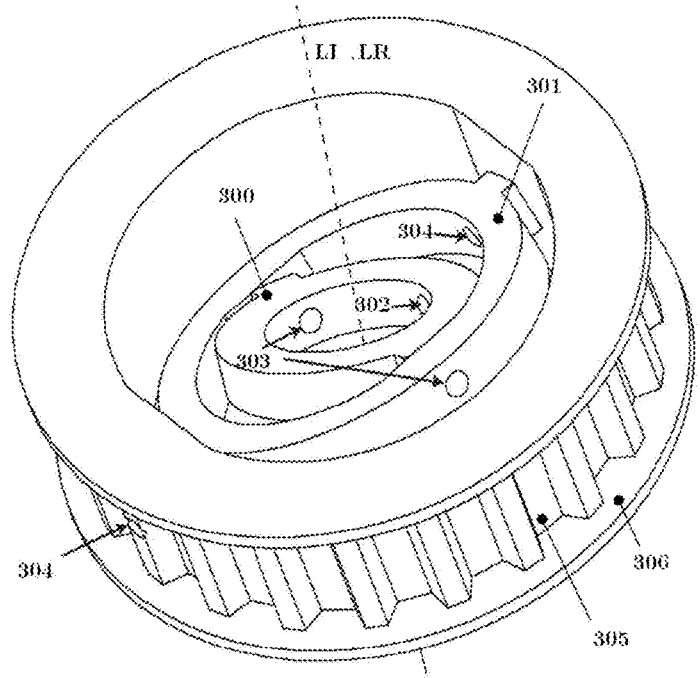

FIG. 32 shows an isometric view of a Cardan-joint one of which is mounted at L10 and one of which is mounted at L12 and which are both connected by a tooth belt to transfer the motion of DOF4 from the proximal member to the instrument as conceptually depicted in FIG. 5.

Figure 33:
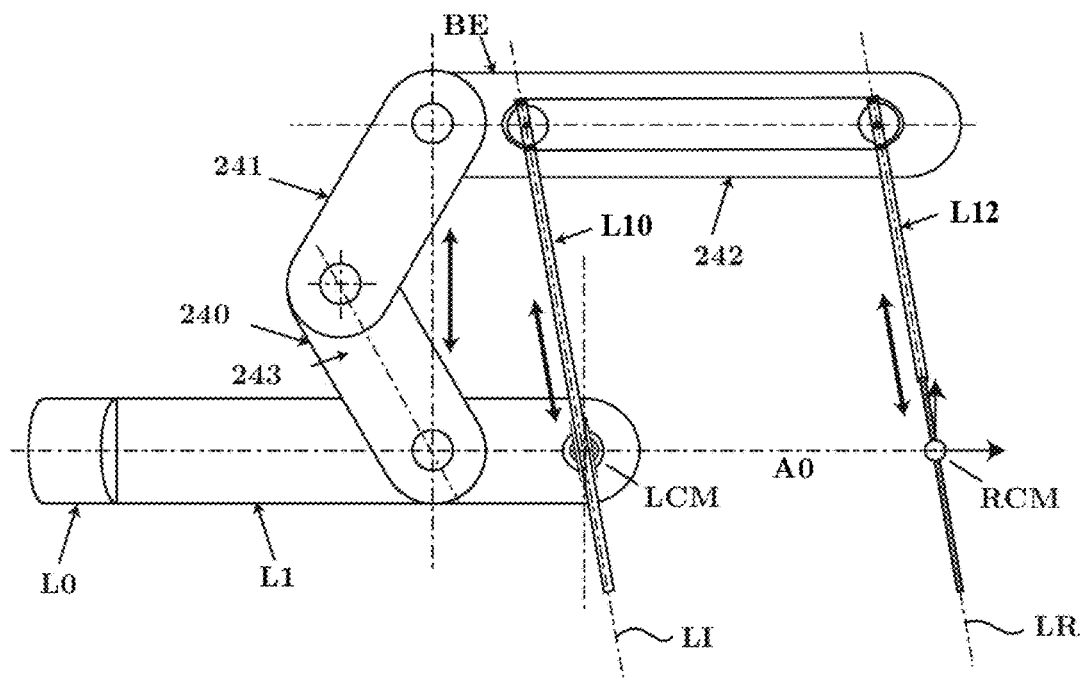

FIG. 33 shows an alternative embodiment of a three DOF RCM mechanism that is achieved by replacing parallelograms through flexible belt drives connected in such way as to guarantee parallelity between input and output axes. The figure shows a belt-drive configuration with similar properties as the described 3DOF RCM mechanism, but potentially increased working range.

Figure 34:
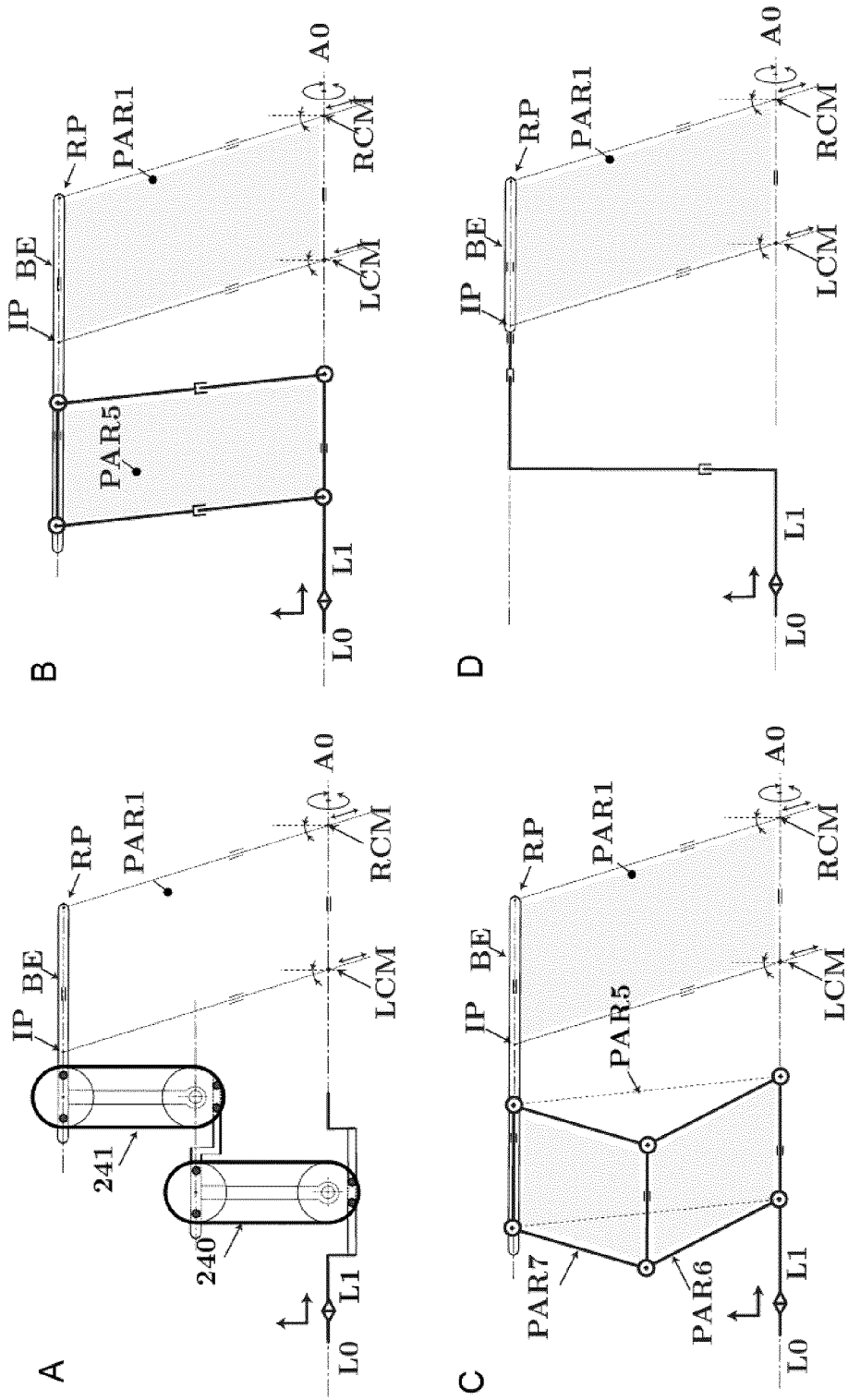

FIG. 34 A-D describe a number of alternative implementations to achieve the two planar degrees of freedom DOF2, DOF3.

Figure 35:
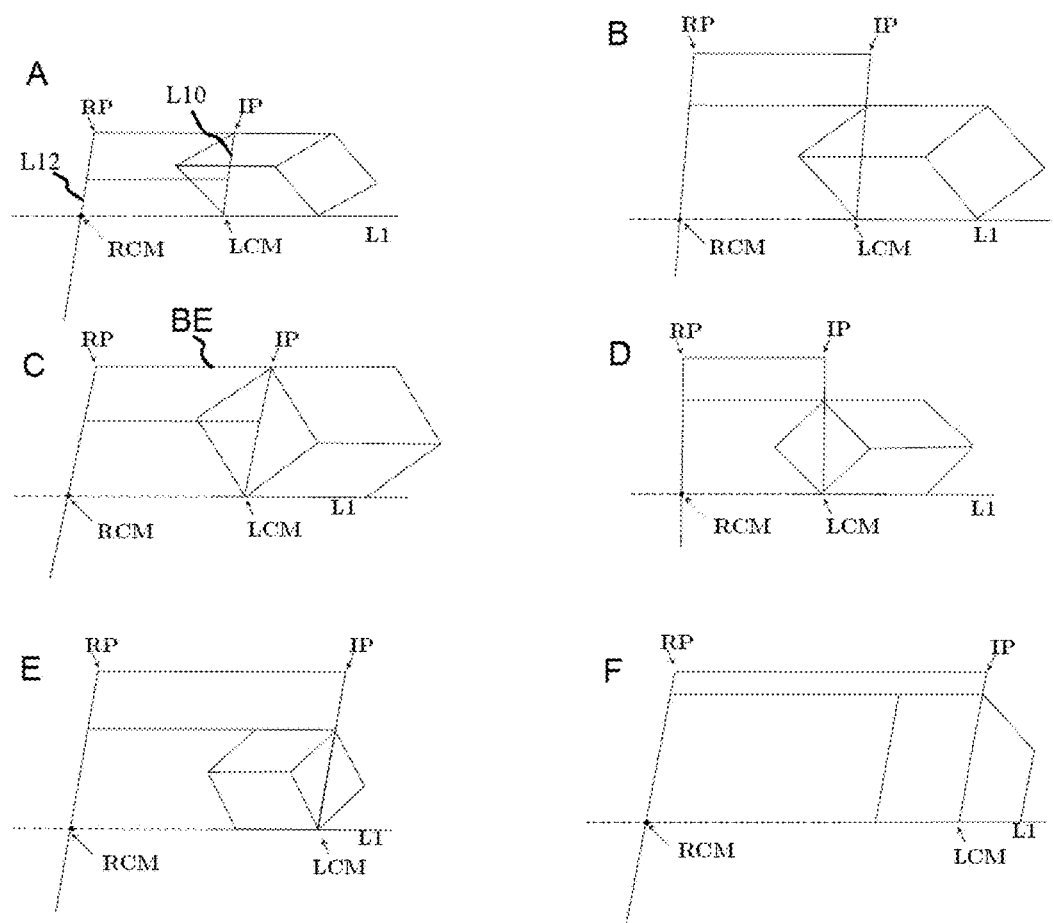

FIG. 35 shows yet another set of possible embodiments A-F of apparatuses according to the invention with two planar degrees of freedom DOF2, DOF3.

DETAILED DESCRIPTION OF THE INVENTION

An important insight that lies at the basis of the proposed invention is that one single parallelogram and a means to position such parallelogram appropriately in space suffices to transfer motion from a local, or proximal, center of motion (which shall be referred to as LCM) to a remote center of motion (RCM). Depending on the mobility of the LCM, depending on the implementation of the single parallelogram and on the implementation of the means to position the single parallelogram appropriately in space, a mechanism can be composed that allows remote positioning of DOF1, DOF2 and DOF3. If additional means are foreseen to transfer the rotation degree of freedom DOF4, all available degrees of freedom DOF1, DOF2, DOF3 and DOF4 can be transferred to the remote instrument. Note that without loss of generality the rotation angles along DOF1, DOF2 and DOF4 will be respectively referred to as roll, pitch and yaw angle in the following.

It is a basic object of this document to disclose several new mechanisms that follow from this principle. The general concept is described below in relation to figures FIGS. 2A-2C, FIG. 3, FIG. 4, FIG. 5 and FIGS. 6A-6C.

FIGS. 2A-2C respectively show an isometric, top and frontal view upon a general layout of such mechanism. One or more of following components can be found to characterize example mechanisms according to the invention:

a base support means, L0, such as base of mechanism 11, adapted to be fixedly mounted to a surface;

a first linkage means, such as base link L1, pivotally mounted on the base support means, L0, for rotation about a first axis A0;

a two-degree-of-freedom mechanism connected to the first linkage means, base link L1. It positions an intermediate point IP with two degrees of freedom in a plane that contains A0 and that rotates together with L1 about this axis. For a strategically chosen geometric point on A0, which will be referred to as the proximal center of motion or LCM, it can be appreciated that an imaginary line LI of constant length can be drawn, extending from the IP and crossing the LCM. This line rotates about LCM and translates inwards and outwards through the LCM upon motion of the IP. Upon rotation of L1 about the mechanism's base, LI will rotate about A0 at the LCM. It can be appreciated that it is the ensemble of these motions, among which two rotational and one linear translational, that is to be transferred to the distal part of the mechanism and more in particular to the mechanism's RCM;

a transfer mechanism (referred to as first mechanism) transfers the motion of LI relative to LCM towards the distal instrument motion, indicated by LR, relative to RCM. The RCM is preferably located on A0 and at a certain distance Δr from the LCM. Hereto, any mechanism (including a real parallelogram) that maintains an imaginary parallelogram PAR1 between LCM, IP, RP and RCM can be employed. This parallelogram is fully determined by the position of LCM, IP and RCM. The remote point, RP, simply completes the parallelogram and is located at the crossing of a line departing from IP parallel to A0 (connecting LCM with RCM) and a line LR starting from RCM parallel to LI. The length of LR is equal to that of LI and is thus adjustable and determined by the position of IP;

an instrument connected to be collinear to line LR rotates about A0 and axis A1 and translates along axis A2 upon changing values of DOF1, DOF2 and DOF3.

Figure 1:
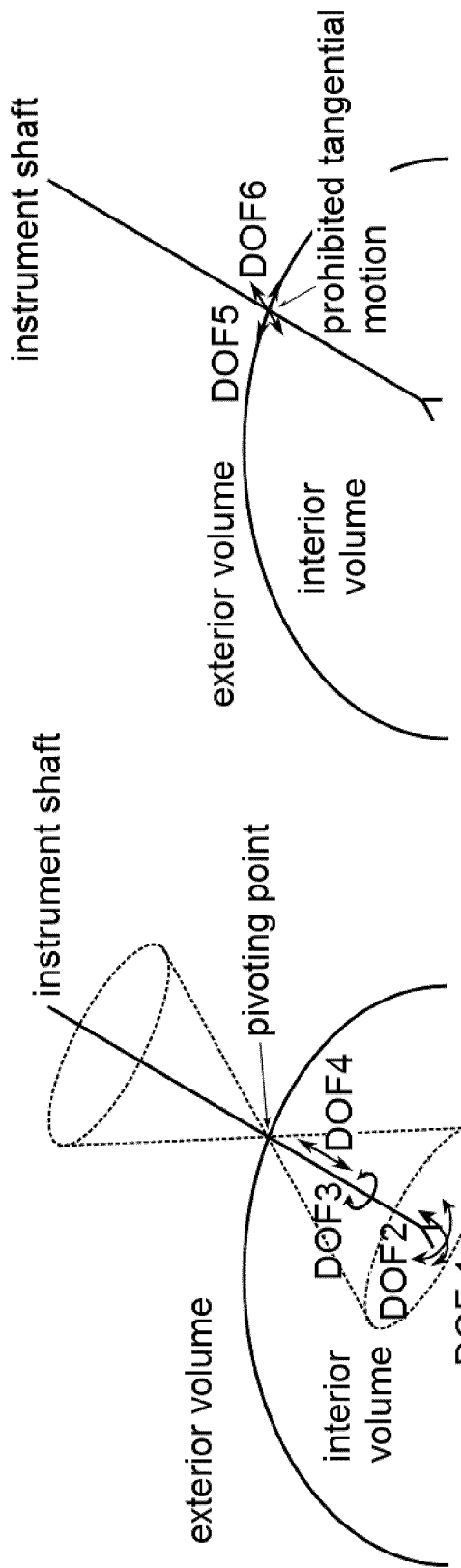
Figure 3:
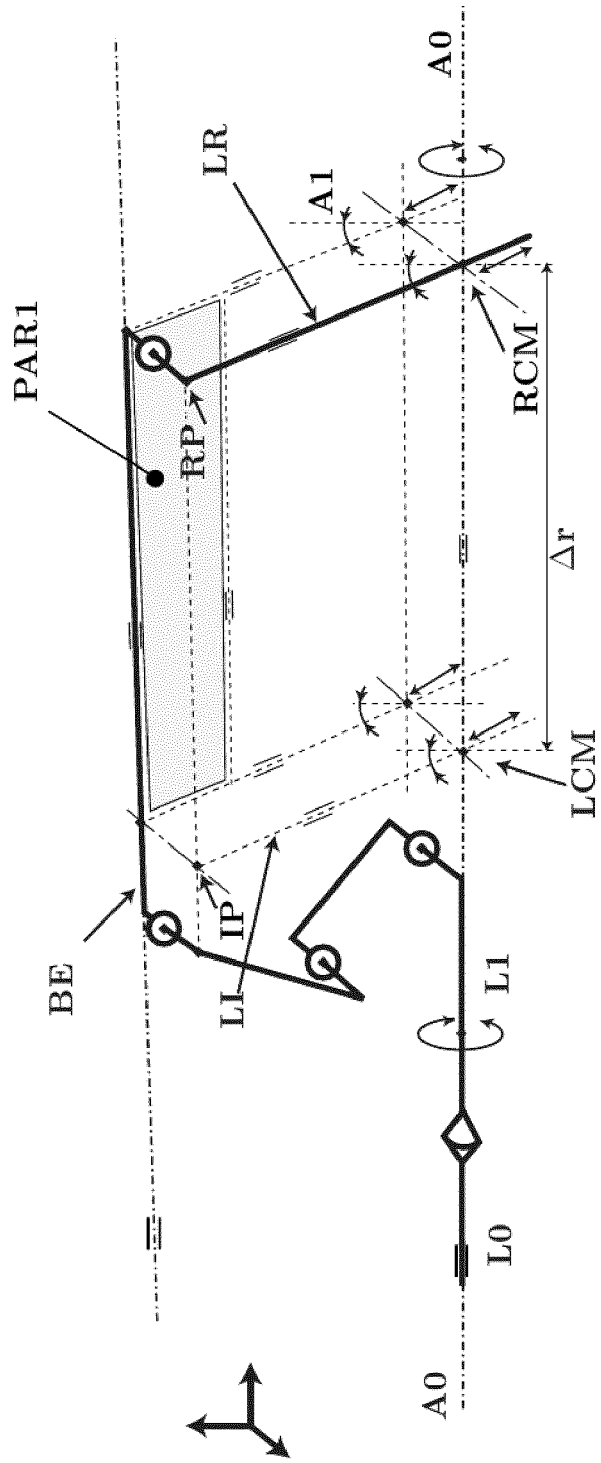
FIG. 3 is an alternative to the in FIG. 2 depicted principle of generating 3 remote degrees of freedom.

In other embodiments of the invention, and referring to FIG. 3, the motion principle can be described comprising following one or more of following components:

a base support means, L0, which is adapted to be fixedly mounted to a surface;

a first linkage means, L1, is preferably pivotally mounted on the base support means, L0, for rotation about a first axis A0;

a two degree of freedom mechanism is connected to the first linkage means L1 and positions an extending bar, BE, with two degrees of freedom on a plane that contains A0 and that rotates together with L1 about this axis, and this so that BE remains at all times parallel to A0. An intermediate point, IP is defined in a constant relative relation to Bar E. For a strategically chosen geometric point on A0, referred to as the proximal center of motion LCM, an imaginary line LI of constant length can be drawn, extending from the IP and crossing the LCM. This line rotates about LCM and translates inwards and outwards through LCM upon motion of the IP. Upon rotation of L1 about the mechanism's base, LI will also rotate about A0 in this geometric point. It can be appreciated that it is the ensemble of these motions, among which two rotational and one linear translational, that is to be transferred to the distal part of the mechanism and more in particular to the mechanism's remote center of motion;

a transfer mechanism (referred to as first mechanism) transfers the motion of LI with respect to LCM towards a distal motion of a distal line LR, with respect to the RCM. Here, the RCM is located on A0 and at a certain distance Δr from the LCM. Hereto, the mechanism maintains a parallelogram between LCM, IP, RP and RCM. Two opposite sides of the parallelogram are formed by A0 and BE. The remaining sides concern LI and LR. The length of LR preferably equals the length of LI and is thus adjustable and determined by the position of IP;

an instrument connected to be collinear to LR rotates about A0 and axis A1 and translates along axis A2 upon changing values of DOF1, DOF2 and DOF3.

From the frontal view in FIG. 2C it can be appreciated that when moving the LCM closer to or further away along the center line, under constant position of the base link L1, together with a varying RCM location, the instrument's pitch angle can be adjusted at wish to map the pitch motion range to the targeted surgical workspace or for example to optimize dynamic properties of the mechanism for a targeted workspace.

According to a preferred embodiment of the invention, the imaginary line LI is materialized through a rigid bar connecting IP with LCM by means of two rotational joints and one sliding joint. In such manner that the connecting bar will advantageously follow the rotational motion of the imaginary line LI closely. Upon motion of translational degree of freedom DOF3 the connecting bar moves through the sliding joint contact and extends more or less at the IP or LCM side, replicating the linear translational motion of LI.

Linkages materializing the imaginary lines LI and LR do not need to be fully straight. As a matter of fact they do not even need to be collinear to the pair of joints of PAR1. In order for a correct motion transfer from LI to LR, it suffices that both linkages have a straight extremity with a length at least spanning the targeted translation range and furthermore that attachments to the corresponding and opposite linkages of PAR1 at the other extremity of these linkages are in such manner that the corresponding joints of these opposite linkages have the same orientation and displacement relative to corresponding selected points belonging to the first extremity of these linkages.

Referring again to FIGS. 2A-2C, the LCM is advantageously consisting of a physical joint with all or a part of the degrees-of-freedom needed to be transferred to the RCM conveniently located w.r.t. the RCM in space. The LCM is advantageously located so that it lies on an imaginary line collinear with A0 and going through the RCM. The LCM is connected to the base support means L0 or any other ground, where the joints and pose of the LCM are organized in such a way as to allow free rotation about an axis collinear to A0 and where an imaginary line LI is moving within the physical LCM joint. A three-degree-of-freedom mechanism, possibly but not necessarily comprising a concatenation of the base link L1 and a two-degree-of-freedom mechanism, advantageously positions the intermediate point IP and with it LI in three dimensional space. A transfer mechanism as described above advantageously transfers the motion of LI with respect to LCM towards the distal instrument motion, indicated by LR, with respect to RCM.

Referring to FIG. 3 showing an isometric view upon an alternative layout of set of mechanisms according to the invention a multi-degree-of-freedom mechanism positions an extending bar, BE in space so that it remains at all times parallel to a line that connects the LCM with the RCM. Such multi-degree-of-freedom mechanism could, but not necessarily does, consist out of a series connection of four rotational joints of which a first joint is collinear with L0 and pivots the multi-degree-of-freedom mechanism about axis A0 passing through both the LCM and the RCM. The intermediate point IP is then connected and defined with respect to BE. A transfer mechanism such as PAR1 maintains a parallelogram between IP, LCM, LI, RP, RCM and LR.

It can be appreciated that the connection bar BE that helps connecting with the instrument, will typically move along the surface of a cylinder that is centered around a line that connects LCM with RCM.

Figure 4:
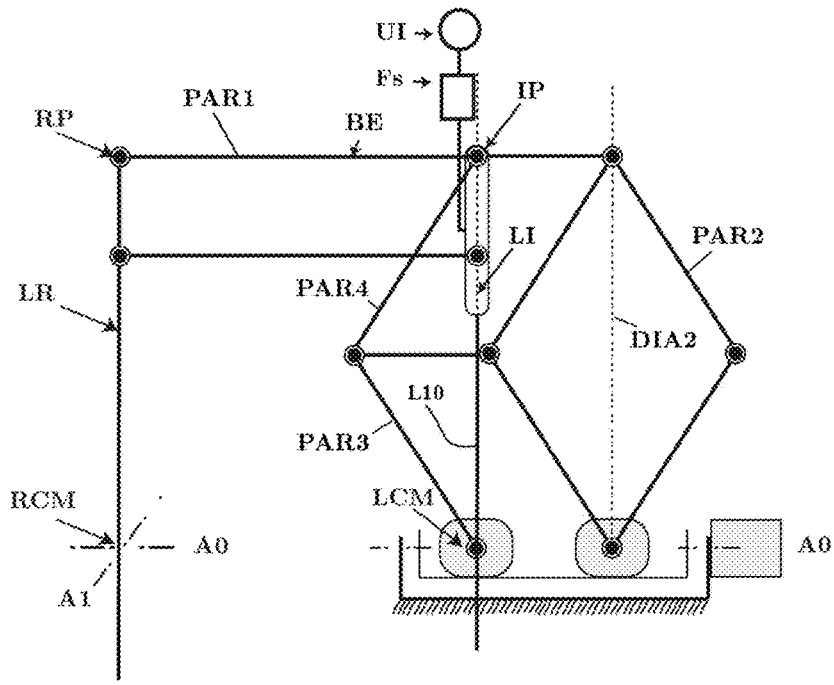
FIG. 4 shows a schematic view upon a possible embodiment providing an example of how the envisioned invention could be foreseen from an intuitive handle that can be used to co-manipulate the device in a synergetic manner.

Referring to FIG. 4, the connecting bar can be extended over a certain constant length at one or both sides, providing a zone where the bar can be gripped e.g. by a human operator. This extension can serve as a user interface UI or kind of dedicated handle at which the operator can interact and co-manipulate the mechanism; providing the possibility to directly influence the DOF1, DOF2 and DOF3 motion of LI which is transferred towards corresponding motion of the LR by a subsequent dedicated mechanism. When embedding a force sensor (e.g. Fs) various types of admittance or impedance controllers can be designed easily to program specific navigation or manipulation assistance schemes (such as e.g. virtual boundaries), or to detect and signal abnormalities amongst others. Note that handles can be foreseen at other parts of the mechanism providing access to single DOFs or to multiple DOFs at once. E.g. also at the level of LR a handle could be foreseen that would provide access to all DOFs.

It will be convenient to note that apparatuses of the invention need not possess any motors and can thus behave as passive devices. In this case, the user can operate the device at a handle attached rigidly on a strategically chosen location on the mechanism. In a preferred embodiment the handle is foreseen to be collinear with LI as described above, or it can be positioned collinear with LR.

FIG. 4 shows an embodiment combining three parallelograms PAR2, PAR3 and PAR4 into a mechanism that guarantees parallel motion of BE related to A0. One can appreciate that the diagonal DIA2 of PAR2 is parallel to LI, however it can be easily observed that the mechanism also works in case the LCM is placed further or closer away from the joint of PAR3. In such case the RCM and work range (pitch angle) will be varied accordingly. Latter property can be used very well to displace the central of the work range away from the vertical (central) angle as it is currently depicted in FIG. 4.

As schematically depicted in FIG. 5, an additional distal rotation degree of freedom, DOF4, about an axis A4 that intersects with A0 and A1 in the RCM can be provided. This rotation degree of freedom DOF4 can be commanded through an actuator placed proximal to the mechanism's base, at the intermediate point IP or installed nearby the end-effector linkage. The mechanisms featuring available degrees of freedom DOF1, DOF2, DOF3 and DOF4 where DOF4 is commanded for example at an intermediate point comprise, in general, following components:

the components of the three-degree-of-freedom mechanism above described and depicted in FIG. 2, with additionally, a third mechanism that connects the rotation of the instrument about LR to for example the rotation about LI of an extension element, indicated as BJ, collinear with LI, an instrument connected to be collinear to LR rotates about A0, A1 and A2 and translates along A2 upon changing values of the available degrees of freedom DOF1, DOF2, DOF3 and DOF4.

LI can be materialized through a rigid bar (not shown) connecting IP with LCM by means of two rotational joints and one sliding joint. In addition a means can be provided to rotate another bar, BJ, also collinear with LI about LI over a certain angle relative with respect to the rigid connecting bar. A dedicated mechanism can be foreseen to transfer this rotation degree of freedom DOF4 to the distal rotation of the instrument about an axis collinear with LR. Such or other mechanisms that work in parallel to such mechanism can be made responsible of transferring the rotational motion of the imaginary line LI and the linear translational motion of the connecting bar towards the rotational and linear translational motion of LR.

In the case the apparatus is a passive device, or otherwise, a handle or user interface is advantageously connected to BJ in which case all available degrees of freedom DOF1, DOF2, DOF3 and DOF4 can be operated through this handle. In other embodiments the instrument itself of a part of the mechanism rigidly connected to the instrument serves as a handle. Other embodiments foresee multiple handles, which can be used to actuate separate or conveniently selected sets of degrees of freedom.

Possibly, a so-called redundant actuation pair can be provided for one or more motion degrees of freedom, wherein the actuation pair comprises a proximally and a more distally arranged actuator. In such case the proximal actuator is responsible for gross motion whereas a small and possibly more distally placed actuator takes care of precise and/or highly dynamic motion in the respective motion degree of freedom. Such configuration is often referred to as a macro-micro configuration.

In apparatuses according to aspects of the invention with rotation degree of freedom DOF4, the rotation about the axis LR can be determined by an actuator and/or brake integrated distally in the mechanism and collinear or parallel with LR, or by a handle parallel with LR, manipulated by a human operator possibly in combination with actuator and brake. In such case no mechanism is needed to transfer rotational motion of LI towards LR.

Robotic components could be used to align the RCM of the mechanism with an entry-point into the body. Such entry-point could be made artificially e.g. by a prior incision by the surgeon, but could equally be a so-called natural orifice. When well-aligned with the incision point, the RCM guarantees that the instrument pivots around the entry-point into the body and prevents exertion of forces in a plane orthogonal to the instrument axis.

In cases where the position of such entry-point is more or less constant over time, the additional robotic component could be used mainly to provide the approach and alignment to the RCM at the onset and to provide retraction at the end of each phase of the intervention. The additional robotic component could also be employed to respond appropriately and support easy retraction in case of emergency situations. Alternatively, apparatuses of the invention can advantageously effect safe retraction without needing to rely on the additional robotic component. One way to achieve such property would rely on a specifically designed gravity compensation scheme whereby the mechanism's rest position lies above the RCM. In such way in case of power cut the mechanism would evolve towards its equilibrium position and retract the instrument outside the patient's body, following this reasoning it becomes clear that for such system only by supplying sufficient torque/power to the actuators the instrument can be brought inside the intracorporeal space.

In cases where the position of the pivot point should be modified online during the procedure the additional robotic mechanism could be made such as to provide this functionality as well.

FIGS. 6A-6C show an embodiment of the current invention positioned upon a position stage allowing to position the PAR1 obliquely to A0. The figure shows how without loss of generality the plane of the parallelogram PAR1 does not need to be parallel to A0 in order for the apparatus to work, as long as the connection between instrument axis LR and the mechanism transferring motion from LCM to RCM is done in such a manner that the instrument axis LR crosses A0 and LR is parallel to the corresponding side of PAR1. In FIGS. 6A-6C it can be seen that the parallelogram PAR1 is obtained by orthogonal projection of LCM, RCM, RP and IP in a plane parallel to the planar (two-degree-of-freedom) motion of LI or LR. The plane of PAR1 can equally be positioned in the plane of motion of LI, or a plane through LCM. As a result, LI and LR will effect identical motion in two parallel planes parallel to PAR1. It will be convenient to note that PAR1 is not parallel to A0 in this case. Apparatuses as the ones shown in FIGS. 6A-6C advantageously allow for creating a workspace above A0 by shifting BE laterally.

Instead of using additional robotic instruments to provide alignment or retraction of the RCM to and from the incision points, the alignment and retraction can also be provided through expansion of the abovementioned mechanisms featuring adjustable link lengths and/or adaptable joint locations. Such can be obtained for example by providing additional means to adjust in equal amounts the length of the links of PAR1 parallel to the axis connecting LCM with RCM. Alternatively, a means to adjust the link length of BE and more in particular adjust the distance between IP and PAR1 can be provided. Alternative embodiments could adjust the position of the LCM w.r.t. L1 or w.r.t. the base L0. When appropriately designed the RCM could be re-positioned in up to three dimensions by adjusting the location of the LCM in up to three dimensions w.r.t. the mechanism base. Yet a further set of preferred embodiments, when appropriately designed, allow adjustment of the RCM, by appropriate adjustment of the link LI. Yet, in a further set of preferred embodiments, the instrument axis is connected to PAR1 via a pair of joints and a pair of additional linkages that are rigidly attached to the corresponding opposite bars of PAR1 that are parallel to A0. By appropriate design of this pair of joints and additional—possibly adjustable—linkages the location of the RCM can be displaced over a certain—possibly adjustable—distance and along a direction perpendicular to A0 and parallel to the plane of PAR1. In a further set of preferred embodiments a similar displacement of the RCM in a direction perpendicular to A0 and parallel to the plane of PAR1 is achieved by a single—possibly adjustable—connection bar at the level of BE that is responsible for displacing the PAR1 in a direction perpendicular to BE and as such of displacing the RCM with an equal amount in the same direction perpendicular A0. In the two abovementioned preferred sets of embodiments the location of A0 is designed appropriately—possibly adjustable—with respect to the driving mechanism so that after above operations the RCM still belongs to A0.

In a set of preferred embodiments of the proposed invention, the mechanism is designed to be as compact as possible and link lengths and pivot positions are in-stalled such that the working volume of the mechanism maps tightly with the space needed to perform the targeted surgical procedure(s). In case different procedures that require different working volumes are targeted, a preferred set of embodiments would allow easy and quick adjustment of links and pivot positions and/or installment and adjustment of mechanical stops, so that the boundaries of the working volume can be set in accordance to the needed working volume. In some embodiments methods that allow automatic verification of the selected stops and workspace can be foreseen.

Gravity balancing elements can be provided in apparatuses of the invention, such as but not limited to fixed or adjustable springs and fixed or adjustable masses that balance the mechanism in some or all available degrees of freedom DOF1, DOF2, DOF3 and DOF4, for different convenient orientations of the mechanism's base with respect to the gravity vector and for different convenient instruments. Such balancing elements can be connected to or embedded into arbitrary but convenient links of the mechanism including, but not limited to LI, L0, the links of the two- or three-degree-of-freedom mechanisms.

In relation to the latter, link lengths, pivots and gravity compensation means can be adjusted in a set of preferred embodiments so as to improve the mechanism's balancing capability or dynamic and manipulability properties and adjust it appropriately to targeted surgical procedures with associated requirements on workspaces.

In a set of preferred embodiments accurate precision is favoured by relying on direct-drive motors and reduction systems that do not introduce play into the structure and subsequently negatively affect the end-effector's positioning accuracy.

Other embodiments were precision is of inferior importance compared to achievable output torque or other specific desirable properties that might be for example implicitly, cost, compactness if relevant and that are equipped with reduction mechanisms that do introduce play, but that do offer adequate output torques or other targeted properties are also included within the set of embodiments covered by this invention.

In relation to the latter, a preferred set of embodiments is designed so that the mechanism is backdrivable against exertion of external moments or of external forces acting at an offset from the remote center of motion. Such set of embodiments are designed to be balanced against gravity over the mechanism's workspace so that upon power failure the mechanism stays in place or moves to a desired and safe region after which, being backdrivable, the preferred embodiment can be manually removed from the patient. Removing the instrument of a mechanism where in particular the linear translational motion is balanced and backdrivable, poses fewer danger for traumas at the entry-point than is the case of mechanisms that have a self-locking property in this linear motion.

Redundant sensing, actuation and/or braking means can be provided so as to provide reliable knowledge and control of the state of the apparatus or links. Such sensing, actuation and/or braking redundancy can be achieved by installing sensing, actuation and/or braking means at the level of the LCM, and/or at the level of the two- or three-degree-of-freedom mechanism.

Robust control methods that maximise predictability and intuitiveness of operation can be used in apparatuses of the invention. Such control algorithms are not limited to control schemes realising simple positioning control, but also span more advanced types of control such as force or impedance control or control schemes designed especially with human robot co-operation in mind. Latter schemes are for example control schemes based on passivity, time-domain passivity or schemes that rely on energy monitoring to guarantee stable behavior of the whole system. Shared control schemes that take over parts of the intervention in an autonomous manner, leaving the user in charge of other parts are expected to prove really helpful too. In general, it is desirable to consider all schemes that support improved human robot co-manipulation or teleoperation.

In a preferred set of embodiments the mechanism is equipped with a versatile interface at its end effector or at intermediate points into the mechanism upon which the instrument or the additional mechanism can be easily attached upon. Such preferred embodiments allow fast and easy attachment of different possibly disposable instruments or simplifies the sterile use of the preferred embodiment.

Apparatuses of the invention can be designed to be backdrivable, direct drive mechanisms possessing high stiffness, relatively low mass and inertia, that achieve high positioning accuracy and are very well suited for use in teleoperation, co-manipulation, shared control or autonomous positioning modes, further being more compact and intuitive than existing mechanisms and provide a clear benefit corresponding to traditional manually executed interventions.

Robotic instruments could be used to provide the instrument with additional local degrees of freedom. After entry into the body these degrees of freedom augment the mobility and manipulability of the instrument tip without affecting the existence of the RCM. Special care is needed to guarantee correct entry, retraction of such instrument and to guarantee its safe use. Actuation of the local degrees of freedom can take place proximally, distally or could happen through some kind of handle or knobs on the extremity of the instrument remaining in the extracorporeal area and thus accessible to the operator.

The different embodiments of the mechanism can be used standalone or in conjunction with other robotic components increasing the available number of DOFs.

Referring to FIGS. 7, 8, 9, 10 and 11 of the drawings, a preferred embodiment of the invention is generally indicated by reference numeral 10. The preferred embodiment can be found to consist of two main parts: a base part of the mechanism 11 depicted in FIG. 12 and a cradle part of the mechanism 12 which is displayed in FIG. 13.

Mechanism Base

The base part of the mechanism consists of a base plate 20 upon which two flanges 21 and 22 are fixedly mounted, 21 at a proximal and 22 at a more distal part of the robot's base. Alignment pins 23 precisely determine the location of the flanges with respect to the base plate 20. A number of fixating bolts 24 rigidly connect both flanges with the baseplate 20.

An actuator assembly is mounted on the proximal flange 21 it consists of motor M0, indicated by 25, connected with four screws 26 to the flange 21. The motor axis is positioned perpendicular to the proximal flange and parallel to A0. The motor axis is placed in the centre of the flange 21 in this embodiment, but other convenient locations can be thought of. The base part is symmetrically built in this embodiment and the plane that can be constructed through the motor axis and A0 acts as a symmetry plane of base part 11. One side of the outgoing motor axis protrudes the flange. A driving pulley 27 is clamped firmly onto this side of the outgoing motor axis. This can be done by a tight fit, by using one or more set screws, or by any other means.

A high resolution encoder 30 is connected to the back side of the outgoing motor axis. A mounting bracket 28 is responsible for the precise relative alignment between motor 25 and encoder 30. The mounting bracket 28 is rigidly connected via four connecting bolts 29 to the flange 21.

The actuator assembly M0 controls DOF1 by orienting the cradle 12 and at the same time the instrument about A0. It can be appreciated that a gearless maxon DC motor RE30 of type 310007 can be used as M0. When a transmission free of play is chosen to adapt the motor torques to the desired range of load torques and provided the cradle possesses few play in addition to a high rotational stiffness about A0, the orientation with respect to DOF1 can be measured accurately by a high precision encoder E0 such as e.g. an R120 incremental en-coder of GPI (Gurley Precision Instruments, US) which generates 65.546 pulses per revolution. The embodiment described here does not include electromagnetic or other breaks nor redundant sensors to control and measure the rotation about A0. Inclusion of such elements can be foreseen in alternative embodiments of the invention.

Through e.g. a capstan cable transmission the actuator torque is transmitted and augmented precisely towards the cradle part 12 of the mechanism. At the same time the cradle will move slower and can be positioned more precisely. The cradle 12 hinges on the pivoting pins 31 and 32. Special care is to be taken in the manufacturing of the different components so that the pivoting pins are aligned in a collinear manner. This includes adhering to adequate tolerances during manufacturing of base plate 20, flanges 21, 22 and the pivots itself. Through the use of precision bearings with inherent small radial and axial play such as those by e.g. GRW (Gebr. Reinfurt Würzburg, http://www.grw.de/) and by applying pre-tensioning techniques, e.g. by pressing bearings with special designed covers 33 against internal collars in flanges; precise and play-free positioning of pivots 31, 32 within the plane of the flanges 21, 22 can be achieved. Through use of lock nuts, such as 34, also play in the axial direction of the cradle, namely along axis A0 can be minimized. In alternative embodiments not discussed in detail here it is possible to replace the cradle by a single joint, allowing further miniaturization of the mechanism and avoiding the need to make opposing pivots collinear. In such case care is to be taken to design the fixation at the level of the single joint sufficiently strong and precise that it resists the gravity, inertial and external forces applied upon the mechanism with minimal deformation at the joint level and maximal stability of the RCM.

Cradle

The cradle 12 consists of a rectangular frame 40 in which at opposite sites of the frame two rectangular cutouts with semi-circular holes are made. Two clamping blocks 41, also foreseen of a semi-circular hole, fit into the rectangular cutouts of the cradle frame 40. When the clamping blocks are fixed via a pair of clamping bolts 42 inside the rectangular frame, each pair of semi-circular holes forms a single circular hole in which the pivots 31 and 32 can be rigidly clamped. Care must be taken that the axes of the two opposing holes are collinear. This can be done e.g. by starting from a full rectangular frame in which first the two circular holes are drilled, after which the clamping blocks are cut out through techniques such as for example wire-EDM. A limited amount of material approximately equal to the diameter of the wire that has been used will be removed during this procedure, just enough to enable a good clamping of the pivots inside of the circular arcs of the frame 40.

The proximal side of the rectangular frame is rigidly connected to the capstan drum 43 of a capstan drive via a pair of bolts 44. The connection of the capstan drum with the pivot 31 is established separately via set screw 45, although this is not strictly necessary. In theory the rectangular frame and capstan drum can be made in one piece, although making them in two can be done faster with less material waste. Also here, care must be taken that the hole in the capstan drum and the hole in the rectangular frame through which the proximal pivot 31 passes are collinear.

Two sets of cable tension block 46 and cable tensioning bolt 47 at opposite sides of the capstan drum 43 are being used to tension the cable of the capstan drive. A through hole foreseen along the central axis of the cable tensioning bolts 47 can be used to pass the cable. The cable is passed first through one hole of a bolt; it is then placed alongside the capstan drum outer arc, winded n times over the capstan pulley 27, and led to the opposite bolt with through hole. Typical values for n are 2 or 3. After tensioning the cable, end clamps can be rigidly fixed at each end of the cable to terminate the cable. Further tightening of the cable can be done by screwing the bolts outwards out of the cable tension block 46. The cable tension block is designed to slide over the capstan drum parallel to A0. For a capstan drum with outer radius R and drum angle α, for n windings of the wire over the capstan pulley with radius r and pitch p, the displacement Δx of the wire in the direction of A0 is:

$$\Delta x = pn + p\frac{R\alpha}{2\pi r}. \quad (1)$$

After adjusting the opposite tension blocks so that their distance along A0 direction equals Δx, the blocks can be fixed to the capstan drum by tightening bolts 48. A guide is milled inside the capstan drum 43 for these bolts to allow the necessary sliding motion of the cable tension blocks 46. The latter are foreseen of a thread in which the bolts can be fixed. The bolts, with heads at the opposite site of the blocks 46, are tightened from the inner side of the capstan.

The two degree of freedom mechanism 49 is assembled into the rectangular frame 43. By clockwise rotation of M0 over an angle θ, the capstan drum, rectangular mechanism and two degree of freedom mechanism 49 will, under absence of play or slip, rotate jointly and in a counterclockwise direction over an angle −iθ about A0, where $$i = \frac{r}{R}. \quad (2)$$

FIG. 14 shows the different elements involved in this motion. For clarity the two degree of freedom is not shown. The actuators and encoders of the latter are connected rigidly to the rectangular frame 12. Hereto two mounting brackets 50 and 51 are foreseen. Each bracket is rigidly connected to the rectangular frame 40 via four connecting bolts 52.

As shown in FIG. 15 it is possible to balance the weight of the mechanism by placing actuators and sensors antagonistically with respect to each other on cradle 12, connected by a common axis that is collinear with respectively A1 and A2. Mounting bracket 50 holds an encoder E1 and motor M2, whereas mounting bracket 51 holds encoder E2 and motor M1. A preferred embodiment of the invention uses the motors in direct drive, avoiding the introduction of play when reduction mechanisms based on gears are used or avoiding additional friction and damping when backlash-free gears are used. In alternative embodiments where geared actuation is used, the antagonistic placement of motor and encoder has the advantage that the rotation about A1 and A2 can be measured directly avoiding errors introduced due to use of gears or other reduction elements. In other embodiments it possible to increase the motor torque output, by employing a playfree transmission such as e.g. a capstan reduction. For an amplification of the motor torque by factor $i_2 = r_2/R_2$ the motors have to be moved along the surface of the bracket by an offset $r_2+R_2$, e.g. towards the respective encoders. Pulleys and capstans can then be conveniently placed at the inner side of the brackets, i.e. between brackets 50, 51 and frame 40.

Care should be taken to align the different components so that A1 is collinear with the axes of E1 and M1. It should further be parallel to A2 which must be collinear with the axes of E2 and M2. Both axes are on their turn (in this preferred embodiment) parallel to A3 about which the sliding guide proximal link L10 pivots. The pivot axes 150 are aligned via bearings 151 and 152 embedded inside the rectangular frame and positioned through the bearing covers 127 and fixating bolts 130. The nuts 153 keep the pivoting axes 150 in place, and allow pre-tensioning bearings 151 and 152 to remove axial and radial play that could be present in the bearings them-selves or in the seating of the bearings into the frame 40.

The top view of the cradle frame, depicted in FIG. 16, gives a clear view on the composition of the connecting axes A1 and A2 indicated with numerals 120 and 140 respectively and the two pivot axes 150 that realise A3. The first connection axis 120 is seated through a pair of bearings 121 and a single bearing 122 in frame 40. The axis extends at both sides outside of 40. At the side of M1 it is connected through coupling 60 to M1. The coupling slides over the axis until set screws inside the coupling are tightened to connect it rigidly to the axis. At the opposite side of the frame the axis has a threaded hole in which a connector axis 126 is screwed into. This axis, collinear with A1, transfers the axis motion to a second coupling 63 which engages with E1. The only torques that are transmitted at this side of the mechanism simply serve to rotate the encoder disk. Torques are thus very low and it is not expected to be necessary to add glue to prevent the screwed axis to unwind during motion of the mechanism. Nevertheless, for safety purpose it can be decided to glue this connection though. Axis 120 carries links L2 and L3.

Special care is taken to establish a precise mounting of axis 120 and of links L2 and L3 that is free of play as this could result into play in the position of the RCM. For example during rotation about A0 when crossing a specific angle, gravity will work in a different direction on the two planar degrees of freedom DOF2, DOF3, causing it to shift suddenly if there remains play in the direction of A1. Axial play in bearings 121 and 122 is removed by pre-tensioning the bearings by tightening lock nuts 123 and 124. The corresponding covers 127 push the bearings against a seating inside the frame 40 hereby positioning 120 at a fixed distance from the surface of 40. A third lock nut 125 is used to fix, via spacer 129, a pair of bearings 128 against a collar of A1. By virtue of this pair of bearings 128, L3 rotates freely around A1. L2 is clamped rigidly to A1 at both sides of the set of bearings 128. The position of L3 along A1 is determined by sliding it against the collar, after which it is clamped.

A similar procedure is employed to mount axis 140 in the frame 40. 140 connects via couplings 61 and 64 to respectively M2 and E2. Lock nuts 143 and 144 are used to pretension bearings 141 and 142. A2 carries L4 which is clamped similar to L2 against here the collar of A2.

2-D.O.F. Planar Manipulator with Actuation at the Base

FIG. 17 gives an overview of the two planar degrees of freedom DOF2, DOF3 mechanism that is hinged upon axes A1, A2 and A3 inside the frame 40. The mechanism consists of a first parallelogram composed out of links L2, L6, L7 and L3, further detailed in FIG. 18. The mechanism further consists of a second parallelogram composed out of links L3, L5, L4 and frame 40 hinged upon axes A1 and A2 and detailed in FIG. 26. A third parallelogram incorporated in the mechanism is formed by linkages L5, L7, L9 and L8. This third parallelogram is depicted in FIG. 27. Its upper linkage L9 extends forwards into the direction of the RCM. Linkage L9 corresponds to the single driving bar BE that drives the single parallelogram between LCM, RP, RI and RCM. Latter parallelogram forms the subject of FIG. 28. Linkage L10 corresponds to the so-called linkage LI; linkage L9 corresponds to BE, whereas linkage L12 collinear to the instrument axis corresponds to LR. Thanks to linkage L11, as depicted in FIG. 28 forming a parallelogram between L10, L9 and L12, the parallelogram PAR1 between LCM, RP, RI and RCM is formed and as such the RCM is realised. FIG. 28 shows the linkage L10 pivoting in frame 40, but in alternative embodiments the pivot can be established independent from frame 40. The different subsystems of the two planar degrees of freedom DOF2, DOF3 mechanism are explained in greater detail below.

A first parallelogram composed out of links L2, L6, L7, L3 and mounted upon A1 is depicted in FIG. 18. As mentioned earlier L2 is clamped rigidly onto A1 by means of a clamping piece 69 and tightening bolts 71. A counterweight 65 is connected with two bolts 67 onto the clamping piece 69. The current counterweight was designed to provide a good gravity compensation for this particular embodiment. Due to the symmetric nature of the entire robot it is placed in the robot's symmetry plane. Adjustable counterweights were masses can be adjusted in three dimensions with respect to the pivot at the intersection of A0 and A1, can be easily connected to 69 or to any other part of the mechanism.

At the other extremity of L2, L2 is clamped onto axis 81 via clamping pieces 70 and tightening bolts 72. Link L6 embeds a number of bearings that allow it to rotate about axis 81. Through a combination of locknuts 88, covers 86 and tightening bolts 89 is the motion of L6 in axial direction constrained and well-determined. At the other extremity L6 is pivoting about axis 84. The position of 84 is further determined by the position of L7 which is rigidly clamped at its both extremities. Clamps 73 and 74 are tightened respectively by bolts 77 and 78 connecting L7 respectively to axis 82 and axis 84. The position of axis 82 is further dependent on the pose of link L3, which is pivoting about 120 and 82 thanks to a set of bearings between L3 and the respective axes. To reduce the effect of the bearing play the bearings are pre-tensioned by a set of covers 87 and tightening nuts 90. Through axes 84 and 82 the parallelogram interacts with the rest of the two planar degrees of freedom DOF2, DOF3 mechanism. L9 is rotating over a pair of bearings 91 about 84. Spacer 99 is used to fix the position of L9 along 84. At 82 the parallelogram connects to L5. L5 rotates about 82 by means of bearings 93. Spacer 99 is used to reduce the play on 93, by pushing on the inner bearing ring in response to a tightened lock nut.

FIG. 19 shows an isometric view of L2 together with clamps 69, 70, tightening bolts 71, 72, counterweight 65 and fixating bolts 67 which are rotating in group about A1. FIG. 19 provides a clear view upon the counterweight 65, which was designed for this preferred embodiment of the mechanism. In particular the requirement not to affect the mechanism's workspace leads to this shape of the counterweight.

FIG. 20 provides a cross sectional view upon the assembly of the different components composing the A1 of the mechanism. In particular it provides a better understanding of how special care is given to pre-tension bearings and to reduce play within the mechanism. At the side of M1, play in bearing 106 is removed by tightening cover 107 and hereby pressing 106 against an inner seating of 40 and by tightening lock nut 109 pushing spacer 108 against the inner ring of bearing 106. At the other side of A1, locknut 112 tightens spacer 111 against the inner rings of the pair of bearings 105. The cover 110 pushes against the outer rings of the bearing pair. Note that no seating is foreseen in the frame 40 at this side. When continuing to tension cover 110 even after the moment that the play in the pair of bearings 105 has been removed, the outer rings of 105 will push through the bearing balls (no more play) upon the inner rings of the bearings and will carry on pushing the entire axis 120 sideways. On its turn, the axis will push through its collar upon the inner rings of 106, reducing the play until the balls of 106 contact the outer rings which are immobilised by cover 107.

L3 is mounted pivotally about axis 120 by the pair of bearings 100. Also here care has been taken to avoid any play and to further determine the position of L3 precisely over the length of A1. This is being achieved by tightening locknut 104 which clamps through spacer 101 bearings 100 against the collar of 120. Through the tightening nut 103 cover 102 is pushed against the outer ring of bearing pair 100, clamping L3 in the direction of A1.

FIG. 21 shows how L4, L5 and L8 are assembled together on a single common axis 162. By screwing the four bolts 79, the clamping blocks 75 pull L8 rigidly on axis 162. L4 which carries the counterweights 66 clamped upon A2 by bolts 135 and as such, rigidly connected to L4, is pivotally connected to axis 162. Also L5 is foreseen of a number of bearings in which axis 162 can freely rotate. Via a number of covers 163 and tightening bolts 166, spacers and lock-nuts 165 the bearings are pre-tensioned appropriately.

L4 and its connection to A2 and counterweights 66 are depicted in FIG. 22. Counterweights 66 are connected through two pairs of bolts 68 to connection piece 134. Latter connection piece has a second function namely to clamp L4 on A2 or 162. A housing 133 for a bearing is foreseen at the other extremity of L4. A pair of half covers 154 is tightened with four bolts 155 in order to pre-tension the bearing that is placed inside. As such rotation of L4 about axis 162 is achieved.

Special care has been taken to assure play-free operation of the rotational motion of the different links L4, L5 and L8. The cross section view FIG. 23 gives a better insight on how this is achieved in a preferred embodiment. L8 is clamped against a collar of axis 83. L5 is rotationally connected to 83 at one side a single bearing 97 is foreseen to this end and at the opposite side a pair of bearings 94. A cover 163 bolted by 166 against the outer ring of 97 clamps the outer ring against a seating inside L5. A lock-nut 165 and spacer 101 are used to clamp the inner ring of 97 against a collar of 83. At the other side of the axis, a similar combination of 165 and spacer 101 are used to tighten the inner rings of the bearing pair 94. A cover 163 and sets of bolts 166 are used to fixate the outer rings of 94. At this site there is no seating foreseen at L5. When tightening 163 strongly, the outer rings of the bearing pair will be forced deeper inside L5 first removing the play in the bearing pair 94, then pushing the entire axis along. Via the collar the axis will push the inner ring of 97 against the bearing balls and those against the outer cover 166. As such all play can be removed effectively.

Another central axis is 82 which joins L3, L5 and L7. FIG. 24 provides an isometric view upon an assembly of axis 82 and links L3, L5 and L7. L3 and L5 can freely rotate about 82. L7 is clamped via bolts 77, 78 and clamping blocks 74, 73 upon axis 82. Nuts 104, 164 and bolts 90, 166 pressing covers 87, 163 are used to keep bearings free of play in their respective housings in L3 and L5.

A more detailed view upon the assembly of the axis is shown in FIG. 25. The figure shows a similar layout for axis 82 as is the case for axis 83. 164 presses spacer 100 against a single bearing 96 which rests against a collar of 82. The cover 163 is bolted by 166 against the outer ring of bearing 96 which is pressed against the seating in L5. At the opposite side, a similar configuration is employed. Nut 164 is screwed via spacer 100 against a dual pair bearings 93 of which the inner ring is clamped against a collar of the axis. Also here, there is no collar that constrains the outer ring of the bearing pair. Instead, just as in 83, play in all bearings can be removed by bolting with 166 the cover 163 against the outer bearing rings and by then pushing respectively the balls of the bearing pair, the inner bearing ring, the axis, the inner bearing ring of the single bearing 96, its bearing balls and finally the outer bearing ring against the bolt cover 166.

The dual bearing pair 92 between 82 and L3 is clamped against the collar of axis 82 by tightening the lock-nut 104 and spacer 102 against the inner bearing ring. Via bolts 90 cover 87 clamps the outer bearing ring against a housing inside L3. By doing so L3 is pivotally connected to rotate around 82 and restrained to slide along it. Note, that the proposed setup allows a limited motion of L3 along the axial direction, namely of the size of the axial play within the bearing. This is not a problem as main function of L3 is to position 82 within the plane of the two-degree-of-freedom mechanism. The correct positioning of the plane of the two-degree-of-freedom mechanism is been taken care of by the clamping with respect to L5. By allowing play at the level of L3 one can lower the manufacturing tolerances which would be rather high in case the same motion would be constrained as several places (e.g. along this axial direction).

FIG. 26 shows an isometric view of the parallelogram mounted into the cradle frame composed out of links L3, L5, L4 and L1. Axes 120, 161, 162 and 140 form the hinges of the parallelogram. The figure shows how lock nuts 164, 165 and 143 serve to preload the inner rings of the corresponding bearings. Each time the load passes through a spacer ring such as 111. In the case of 120 the ring slides over the small connection axis 113 that is collinear to axis 120 and is screwed into this axis 120 with the purpose to attach the encoder to the axis. 114 is a triplet of drill holes to attach covers like 163 through bolts such as 166 and apply preload upon respective bearings or pairs of bearings. For the joints between L3 and L5 and L4 and L5 respectively, each time four (two times two) holes need to be drilled into L3 and L4. These drill holes allow attaching pairs of half covers and as such tensioning the bearings inside L3 and L4. Here half covers allow for easier assembly of these covers.

FIG. 27 provides an isometric view upon the parallelogram composed out of links L5, L7, L9 and L8. Links L7 and L8 are clamped upon axes 82, 83 at one extreme and upon 84 and 85 at the other extreme.

Clamping blocks 73, 75, 74 and 76, fixate L7 and L8 upon the respective axes. Clamping blocks can be made by wire-EDM (Electro-Discharge Machining), starting from one single cube the contours of the combined clamping blocks and links 73, 74 and L7 at one side and 75, 76 and L8 at the other side are milled or wire-EDMed. Next, through holes are drilled, after which the clamps are cut out (wire-EDM). The material loss from the passage of the EDM wire will be uniform over the cut trajectory and ensure a good and tight clamping around the axes. In a next step the H-shape is carved out of from the link block. Also here, typically wire-EDM is used as it does not lead to deformations of the material.

The ensemble of H-form and respective clamps are slid over the respective axis until a certain collar upon the axis, in this way the axial position of these links is uniquely determined. At this point, bolts 77, 78, 79 and 80 are tightened and the parallelogram is formed. Bearing pairs 92 and 94 can be seen on axis 82 and 83. These are the places where links L3 and L4 attach onto this parallelogram. The pair of bearings 95 can be seen on axis 84 where L6 comes in into this mechanism. The spacer 98 is used as an intermediate part to pre-tension the inner side of the bearings. Finally, note that L9 appears here as an upper bar extending out of one side of this parallelogram in the direction of the mechanisms end-effector. Note, that this functions as a single bar connecting the two planar degrees of freedom DOF2, DOF3 mechanism that connects and steers the parallelogram that positions the instrument.

FIG. 28 provides a view upon the distal parallelogram that transfers the motion around the LCM towards instrument motion around and through the RCM. The distal parallelogram composed out of the instrument holder L12, links L10, L11 and L9, is positioned in 3D space through the single steering link L9. In the preferred embodiment in FIG. 28 the LCM is embedded into the cradle frame 40, in alternative inventions a spherical sliding joint can be positioned independent from the cradle frame.

Axes 184, 186, 187 and 185 form the pivots of the parallelogram. The axes 186 and 187 these axes consist out of two parts, namely a pair of collinear axes in between which the instrument holder L12 is clamped. Instruments such as 170 can be easily inserted into the instrument holder. Other preferred embodiments would have an instrument holder that can be separated easily along a plane parallel to the instrument axis, allowing to cover the robot and part of the instrument holder by a surgical drape and as such facilitate the maintenance of a sterile operating space.

The pairs of axes 186 and 187 rotate in bearings embedded in L9. Play in the bearings is removed by pre-tensioning these bearings with lock nuts 172, covers 173 that are tightened with bolts 174. Axes 184 and 185 are clamped by clamps 188 and 189 upon L9. Two bearing pairs inserted into 192, the upper part of L11, allow the latter to pivot with respect to links L9 and L11. The clamps are tightened by bolts 190 from above L9 and by bolts 191 from below L11 so as not to reduce the workspace needlessly e.g. when folding the parallelogram.

The entire parallelogram can rotate and slide in and out along L11. 181 serves here as a pivot guide that is hinged at axis 150 in the cradle frame 40. In the current implementation the pivot point is embedded within the cradle frame, but as mentioned earlier in other embodiments the pivot can be made standalone, in such case it suffices to construct a spherical sliding joint and locate it at the desired LCM position in space. Axis 150 also consists out of a pair of collinear axes which are revolving around bearings embedded in 40 and tightly connected to the pivot guide 181 by two pairs of set screws that lock the axes upon 181. L11 and more in particular the bar 180 slides through the pivot guide, a linear bearing is hereto embedded into 181. The cover 182, tightened by four bolts 183 is used to constrain the pose of this bearing. The rotary bearings in the cradle frame are pre-tensioned by a pair of covers 127, lock nut 153 and tightening bolts 130.

FIG. 29 shows an isometric view upon proximal link L10 inserted into the pivot guide 181. The pivot guide is rotating about A3, in concrete axes 150 that are inserted into the holes 197. The axes 150 are rigidly connected to 181 by tightening set screws 200. L10 consists out of two parts. 192 is a connection block that forms one side of the parallelogram L12, L10, L11 and L9. It is foreseen of a milled hole in which bar 180 fits. A pair of set screws 196 is used to fix 180. 180 is aligned to the symmetry axis of 192. Bar 180 slides in and out through a pair of linear bearings embedded inside the sliding block 181. The cover 182 tightened by four bolts 183 is used to constrain the pose of the lower linear bearing. At the other extremity, axes 184 and 185 pass, supported by a pair of radial bearings embedded inside 192, through the connection block. Two pairs of covers 194, bolted with 195 and lock nuts 193 are used to pre-tension these radial bearings.

FIG. 30 shows two cross sectional views upon L10 providing better insight on the assembly of L10 and the layout of the different elements belonging to this link. The left part of FIG. 30 shows a cross sectional view upon L10 from a section plane parallel to the symmetry-axis of L10 that coincides with the surface of 181. From top to bottom cross sections of links L9, L11 and L1 (element 40) can be seen. The figure shows how 193, 194 and 195 responsible for tensioning the radial bearings of 192 are positioned between the slide block 192 and links L9 and L11. The lower part shows the connection of the pivot guide 181 with 40 via axes 150 through a combination of cover 127, tightening bolts 130 and lock nuts 153.

The right part of the figure shows a cross-section parallel to the previous one, but at the level of L10's symmetry-axis. The figure shows the assembly of 192 at the level of axes 184 and 185. Two pairs of radial bearings 202 allow free rotation about 184 and 185. It can be seen how lock nuts 193 put the inner rings of the bearings 202 under tension via respective spacers 203.

Whereas the outer bearing rings are tensioned through covers 194 and respective bolts 195. Only at one side does the outer bearing rest against a collar inside 192. The opposite does not possess such collar. As a consequence, when tightening cover 194, first, the play in the first bearing will be removed, after which the entire axis is pushed through the second bearing against the opposite cover 194. The play in this part of the mechanism is as such effectively removed.

The lower part of the figure shows the linear bearings 201, the pair of axes 150 connecting 181 with 40. Axes 150 pivot about a double pair of bearings 198 inside 40. The lock nuts 153 are used to pretension the bearing inner rings via spacers 199. Play is removed in a similar way by tensioning between the pair of bearing covers 127.

The left part of FIG. 31 provides a frontal view upon a surgical instrument 170 inserted into the instrument holder 171. The position of 171 in space and thus also of 170 is determined by the pair of links L9 and L11. The extremity of both L9 and L11 take in this embodiment a U-like shape. In other embodiments single-sided attachments could be easily envisioned. The former provides higher stability and rigidity, whereas latter approach could allow more compact and more easily attachable/detachable solutions. The instrument holder is pivotally clamped in between the two sides of the U by two pivoting axes. Each pivoting axis is rigidly connected to 171 by a corresponding setscrew 176 and rotates around a bearing embedded inside one arm of the respective links L9 or L11.

The right part of FIG. 31 provides a cross-sectional view upon the instrument and instrument holder. The figure shows how 171 is pivoting around L9 and L11 via two pairs of axes 186 and 187 respectively that are each supported by pairs of bearings 175 tightened via spacers 177, nuts 172, covers 173 and tightening bolts 174.

FIG. 32 provides an isometric view upon a dedicated cardan coupling that is designed to transfer the rotational motion of DOF3 from an axis collinear to line LI towards the instrument and towards the rotational motion of the instrument about the axis LR. For this to work a similar dedicated cardan coupling is connected both at an extremity of LI e.g. by means of an extension that is clamped to the connection block 192 and at an extremity of LR e.g. by means of an extension connected to body 171. Whereby both extensions incorporate a rotational component that rotates about an axis parallel to respectively LI and LR and whereby in the case of the extension part at the level of LI force/torque sensors and/or rotational actuators can be embedded and aligned appropriately inside the extension block, and whereby in the case of LR the instrument is connected to this axis so that upon rotation of the cardan, the instrument rotates about its axis. In combination with a timing belt the two dedicated cardan couplings allow transferring rotational motion DOF3 in a manner that is independent from the motion along DOF1, DOF2 or DOF4. Hereto, the dedicated cardan couplings must be attached at a same distance with respect to BE upon the axial part of the respective connection blocks.

This happens by attaching the inner rings 300 via a pair of setscrews 302 to the axial part of the connection block. The middle ring 301 of the cardan coupling is able to pivot about the axis 303 in the inner ring 300. The outer ring 305 on its turn will be able to pivot about a pair of axes 304, perpendicular to 303, inserted into the central ring 301. The outer ring 305 has a toothed surface in which a timing belt can engage upon. The pair of flanges 306 at opposite sides of 305 prevent the timing belt from slipping away from the 305 surface. This dedicated cardan coupling as such installs a 2DOF passive joint at the links LI, LR. The passive joints together with the connecting timing belt ensure that the timing belt remains under all combinations of DOF1, DOF2 and DOF4, parallel to BE, whereas the 3thd DOF namely the rotation about LI will be transferred precisely via the timing belt to LR.

OTHER EMBODIMENTS

Without wishing to be exhaustive, a number of alternative embodiments according to aspects of the invention are provided below.

Alternative embodiments employing flexible belts as described by Jensen in U.S. Pat. No. 5,817,084 can be used conveniently to derive particular embodiments that potentially have a broader working space since less internal collisions between different linkages of the mechanism might occur and/or that are more compact compared to implementations where a plurality of rigid linkages are employed to establish a parallelogram between those linkages.

An example of such embodiment incorporating flexible belts is depicted in FIG. 33. This figure shows an alternative embodiment of a three DOF RCM mechanism that is achieved by replacing parallelograms through flexible belt drives connected in such a way as to guarantee parallelism between input and output axes in a similar way as a parallelogram does. The figure shows a belt-drive configuration with similar properties as the described 3DOF RCM mechanism, but potentially increased working range.

Belt drives 240 and 241 position BE in two degrees of freedom w.r.t. L1 while keeping BE parallel to A0 which is, as depicted in FIG. 33, collinear to L0, L1 and connects the LCM with the RCM. Bar BE connects the two-degree-of-freedom mechanism with linkage LI, here a straight linkage that slides in and out and rotates about the LCM. The current figure shows the configuration in its neutral position which is slightly tilted given the difference in distance between the pivoting points of LI w.r.t. the respective joints of the two-degree-of-freedom mechanism. It can be observed here as well that by adjustment of the distance between LCM and the lower joint of the two-degree-of-freedom mechanism the RCM can be repositioned as well as the central angle in the pitch working range. A third flexible belt driver 242 is embedded within linkage BE. This belt drive realises parallelism between LI and LR. Finally, a simple belt transmission 243 can be embedded within the belt driver 240 so that the actuation of 241 can be installed at the level of L1 and transferred with minimal additional inertia to 241.

It can be appreciated that any combination of belt drives with combination of parallelograms based on linkages can be employed to create the presented 3DOF motion.

It can be easily seen that this mechanism can be equally and easily expanded to a 4DOF mechanism with additional actuation of the instrument about its own axis.

FIG. 34 describes a number of alternative implementations to achieve the two-degree-of-freedom mechanism providing two planar degrees of freedom DOF2, DOF3. The presented examples all ensure parallelism between the linkage BE and an axis connecting the LCM with the RCM. Note that the figure further makes abstraction of the linkages attached at the other extremity to BE; it basically assumes that a certain practical configuration is foreseen that maintains the parallelogram PAR1 between LCM, BE and RCM. The schematic picture does not draw the particular part of the embodiment responsible of achieving PAR1. Furthermore, FIG. 34 assumes that this two-degree-of-freedom is mounted upon a link L1 that is rotating pivotally about L0 and does not introduce three-degree-of-freedom mechanism that generates a similar motion of BE, namely 3DOF motion parallel to the imaginary line connecting LCM to RCM, although such three-degree-of-freedom mechanisms could be easily designed and drawn and therefore are considered to be included amongst the different embodiments associated to the invention.

FIG. 34 A shows a particular embodiment of the two-degree-of-freedom mechanism making use of two flexible drives 240 and 241 to position BE in two dimension and parallel with respect to A0.

FIG. 34 B shows a particular embodiment of the two-degree-of-freedom mechanism where the position of BE is realised by a de-formable parallelogram PAR5 such as one described in U.S. Pat. No. 5,397,323 Note, that this particular embodiment differs from the one described in U.S. Pat. No. 5,397,323 as by virtue of the LCM it becomes possible to orient the instrument in a manner that is not parallel to the pair of opposite linkages of PAR5. It can be observed that this property is achieved by installing IP at the distance to the closest pivot of PAR5 that differs from the distance of the LCM to the corresponding closest pivot of PAR5. By adjusting this distance the RCM and workspace of the mechanism can be tailored towards a specific surgical task.

FIG. 34 C shows corner a particular embodiment of the two-degree-of-freedom mechanism where the position of BE is realised by a pair of parallelograms PAR6 and PAR7. It can be appreciated that the combined pair of parallelograms effectively creates a deformable parallelogram PAR5 that corresponds to parallelogram PAR5 in the embodiment sketched in the upper right of the figure. Compared to the latter, this embodiment does not require two parallel linear slides or actuators. It can be simply actuated by rotary actuators, both possibly mounted at L1 if a connection belt is foreseen in a similar fashion as described in FIG. 34.

Finally, FIG. 34 D shows an embodiment where the two-degree-of-freedom mechanism is generated by a pair of orthogonally placed linear actuators or linear slides. Note, that this orthogonality is not necessary. In fact, any convenient from 0 and π differing angle between the two linear actuators/slides is allowed as long as the connection pieces with linkages L1 and BE are angulated appropriately so as to keep BE parallel to L1.

FIG. 35 A-F show yet another set of possible embodiments of the planar-mechanism. This figure proposes a number of alternative ways on how to connect the two-degree-of-freedom mechanism to the single parallelogram RCM-LCM-RP-IP closest to the mechanism's end-effector. Note that the link connecting IP and LCM, parallel to the distal link L12 is L10. Although not drawn in this figure it should be understood that the link L10 has a fixed and sufficiently long length and that it passes deeper and deeper through the LCM when the distal link L12 moves further downwards. In an alternative embodiment the sliding joint through which link L10 passes is mounted at the level of BE. In the latter embodiment L10 does not move downwards while moving the instrument deeper, instead it will protrude more and more BE from above as latter BE and parts of the driving mechanisms are lowering together with the instrument.

FIG. 34 and FIG. 35 demonstrate variations in the two-DOF-mechanism that are mounted on a pivoting axis L1. Similar variations and alternative embodiments are included within this invention that generate a three-DOF-motion by an appropriate possibly redundant combination of rotary and linear actuators, linkages and slides so as to position BE in three-degrees-of-freedom w.r.t. a line connecting LCM with RCM.

As indicated in the different general descriptions of embodiments of the invention such as depicted amongst others in FIG. 2, FIG. 3, FIG. 5, FIG. 4, FIG. 6 and FIG. 34, the invention foresees in any means that establishes a single deformable parallelogram between LCM, RCM, RP and IP to transfer the motion from LI to LR. As indicated for this to work neither LI nor LR need to be straight, only a certain part on these links that is to pass through the LCM or through the RCM needs to be straight. The only additional condition is that an imaginary line that can be drawn between LCM and the associated pivot between LI and BE has equal length and orientation as an imaginary line that can be drawn between the RCM and the associated and opposite pivot between LR and BE. While all configurations meeting the abovementioned conditions suffice, one particular implementation is thought to be of particular interest; being an embodiment where at the level of the LCM the sliding bar slides within a bushing that is mounted tangentially to a rotary joint with non-zero radius r creating as such a two-dimensional joint with an offset r at the level of the linkage LR, the linkage consists out of a shape generating an offset of r distance between a parallel part to the instrument connected between the two joints of the single parallelogram at the side of LR and LR itself. In such way additional space can be created in front of the single parallelogram where only the single linkage LR is existing.

Another particularly interesting embodiment connects LR not directly with the linkage between the two joints of the single parallelogram, but rather foresees a pair of two additional joints that are mounted at a certain and equal distance h perpendicular to and with respect to BE and the opposite link of the single parallelogram. This organisation allows one to have the RCM located at a similar distance h and in the same direction from the LCM. For multi-DOF RCM systems the other DOFs must be organised to also create motion about the displaced RCM point.

From the foregoing description, it will thus be evident that the present invention provides a design for a mechanism realising up to 4 remote degrees of freedom. As various changes can be made in the above embodiments and operating methods without departing from the spirit or scope of the following claims, it is intended that all matter contained in the above description or shown in the accompanying drawings should be interpreted as illustrative and not in a limiting sense.

Variations or modifications to the design and construction of this invention, within the scope of the appended claims, may occur to those skilled in the art upon reviewing the disclosure herein. Such variations or modifications, if within the spirit of this invention, are intended to be encompassed within the scope of any claims to patent protection issuing upon this invention.

Embodiments of the present invention can be enhanced, by means not restricted to the ones described below:

incorporation of a force measurement mechanism to measure the interaction forces exerted by the instrument with the object of interest, without disturbance caused by frictional forces, such as those generated by translational motion through the trocar;

incorporation of a force measurement mechanism to measure the interaction forces exerted by the mechanism upon the body wall so as to notify whether the RCM is still correctly aligned and if needed automatically adjust or signal a warning to adjust and/or indications on how to adjust the position of the RCM;

incorporation of instruments with local degrees of freedom and embedding of actuators away from the end-effector through a combination of cables or other transmission means.

NUMBERED LIST OF COMPONENTS INDICATED IN DRAWINGS 10 preferred embodiment with 3 degrees of freedom
11 mechanism base
12 cradle part of mechanism
20 base plate
21 proximal flange of base
22 distal flange of base
23 aligning pins
24 flange fixating bolt
25 driving motor
26 motor fixation bolts
27 driving pulley for capstan
28 mounting bracket encoder
29 encoder mounting fixation bolts
30 incremental encoder measuring motor zero position
31 proximal pivot of base
32 distal pivot of base
33 tightening cover bearings of base pivots
34 lock nut of distal pivot
40 cradle frame
41 pivot clamp block
42 pivot clamp block bolts
43 capstan drum
44 capstan connection bolt
45 set screw for capstan fixation on A0
46 cable tension block
47 bolt with through hole for cable tensioning
48 bolt for fixing cable tensioning block
49 two degree of freedom mechanism
50 mounting bracket for E1 and M2
51 mounting bracket for E2 and M1
52 mounting bracket connecting bolt
60 M1 coupling
61 M2 coupling
62 bearing for A1 in craddle
63 E1 coupling
64 E2 coupling
65 counterweight1
66 counterweight2
67 counterweight1 fixating bolts
68 counterweight2 fixating bolts
69 lower clamping piece on L2
70 upper clamping pieces L2
71 clamping bolts lower clamping pieces L2
72 clamping bolts upper clamping pieces L2
73 lower clamping pieces L7
74 upper clamping pieces L7

75 lower clamping pieces L8
76 upper clamping pieces L8
77 clamping bolts lower clamping pieces L7
78 clamping bolts upper clamping pieces L7
79 clamping bolts lower clamping pieces L8
80 clamping bolts upper clamping pieces L8
81 connecting axis between links L2 and L6
82 connecting axis between links L3, L5 and L7
83 connecting axis between links L4, L5 and L8
84 connecting axis between links L6, L7 and L9
85 connecting axis between links L8 and L9
86 tightening cover bearings of L6
87 pair of tightenings half covers enclosing bearings of L3
88 lock nuts of L6
89 tightening bolts of L6 cover
90 tightening bolts of L3 cover
91 dual bearing for L9 connection on 84
92 dual bearing for L3 connection on 82
93 dual bearing for connecting 82 on L5
94 dual bearing for L4 connection on 83
95 dual bearing for L6 connection on 84
96 single bearing for connecting 82 on L5
97 single bearing for connecting 83 on L5
98 spacer between L6 and L7
99 spacer between L6 and L9
100 spacer between L3 and L5
101 spacer between L4 and L5
102 spacer on 82 to position L3
100 bearing pair carrying L3 on A1.
101 inner bearing ring fixation on L3
102 cover fixating outer part of central bearing pair between L3 and A1.
103 tightening nut for fixation cover on outer part of central bearing between L3 and A1.
104 fixating nut for fixing bearing on L3
105 bearing pair between A1 and cradle frame
106 single bearing between A1 and cradle frame
107 cover fixating outer part of bearing between cradle frame and A1.
108 ring fixating inner part of bearing between cradle frame and A1.
109 nut fixating inner part of bearing through fixating ring.
110 cover fixating outer part of bearing between cradle frame and A1.
111 ring fixating inner part of bearing between cradle frame and A1.
112 nut fixating inner part of bearing through fixating ring.
113 connecting rod between A1 and encoder
114 triplet of drill holes to attach a cover and fixate the outer ring of a (pair of) bearing(s)
120 driving axis of A1
121 first bearing of A1 in cradle frame 40
122 second bearing of A1 in cradle frame 40
123 lock nut, to remove axial play along A1
124 lock nut, to remove axial play along A1
125 lock nut, fixing bearings on A1
126 connection axis between coupling and A1
127 bearing cover
128 dual bearing for A1 and L3
129 spacer on A1
130 cover fixating bolt
131 bracket connecting bolt
132 set screws to fixate counterweight)
133 bearing chamber of L4
134 counter weight holder part of L4
135 connection bolts connecting link and counterweight part of L4
140 driving axis of A2
141 first bearing of A2 in cradle frame 40
142 second bearing of A2 in cradle frame 40
143 lock nut, to remove axial play along A2
144 lock nut, to remove axial play along A2
145 lock nut, fixing bearings on A2
150 slider holding axis
151 first bearing of A3 in cradle frame 40
152 second bearing of A3 in cradle frame 40
153 nut to fixate bearings on slider holding axes
154 half cover to pretension bearing
155 half cover tensioning bolts
160 half cover to pretension bearing
161 connecting axis between links L3, L5 and L7
162 connecting axis between links L4, L5 and L8
163 tightening cover bearings of L5
164 lock nut, fixing bearing on 161
165 lock nut, fixing bearing on 162
166 tightening bolts of L5 cover
167 distance spacer on A1
170 instrument
171 instrument holder
172 lock nuts to fix bearings on L9 and L11
173 covers to pretension bearings on L9 and L11
174 tightening bolts of L9 and L11 covers
175 bearing pairs for instrument holder
176 instrument holder fixating screws
177 inner bearing ring fixation
178 set screw to fixate instrument
180 axis sliding in linear guide
181 pivoting guide for linear slider
182 tightening cover for bearings in pivoting guide
183 tightening bolts for guide cover
184 connecting axis between links L9 and L10
185 connecting axis between links L10 and L11
186 connecting axis between links L9 and L12
187 connecting axis between links L11 and L12
188 clamp block, connecting 184 to L9
189 clamp block, connecting 185 to L11
190 clamp block 188 connecting bolts
191 clamp block 189 connecting bolts
192 sliding axis housing forming parallelogram between L9, L12 and L11
193 lock nuts to fix inner parts of bearings on 184 and 185
194 covers to pretension outer part of bearings on 184 and 185
195 tightening bolts of 194 covers
196 set screw to fix linear guide in 192
197 hole for inserting 150
198 dual bearing support of pivoting axis
199 spacer for clamping inner part of 198
200 set screws for fixating axes 150
201 pair of linear bushings guiding translation axis
202 set of bearings for mounting L10 pivotally into 192
203 spacer for clamping inner part of 202
240 first flexible belt drive, realising parallelity between input and output connection bars
241 second flexible belt drive, realising parallelity between input and output connection bars
242 third flexible belt drive, realising parallelity between input and output connection bars
243 simple belt to transmit motion to remote joint
300 inner ring of cardan coupling
301 middle ring of cardan coupling
302 set screws
303 pivot axis middle ring 301
304 pivot axis outer ring 305

305 outer ring of cardan coupling
306 flanges

The invention claimed is:
1. An apparatus for generating motion around a remote center of motion, comprising:
   a distal link arranged to revolve about the remote center of motion and to translate through the remote center of motion;
   a proximal link arranged to revolve about a proximal center of motion through a rotational joint and a sliding joint to effect rotation about an axis of rotation comprising the proximal center of motion and to effect translation relative to the proximal center of motion in a plane of motion of the proximal link that is perpendicular to the axis of rotation;
   a base link adapted to be coupled to a mechanism base, wherein the proximal center of motion is coupled to the base link;
   a first mechanism comprising a first link pivotally coupled to the proximal link and to the distal link, wherein the first link and the proximal link are arranged to pivot relative to each other about a first pivot axis, wherein an intermediate point is defined on the first pivot axis, and wherein the first link and the distal link are arranged to pivot relative to each other about a second pivot axis, wherein a remote point is defined on the second pivot axis, wherein the first mechanism is operable to transfer motion of the proximal link relative to the proximal center of motion to a motion of the distal link relative to the remote center of motion by maintaining a parallelogram between orthogonal projections of the proximal center of motion, the distal center of motion, the intermediate point, and the remote point on the plane of motion of the proximal link, wherein a length between the intermediate point and the proximal center of motion is adjustable;
   a second mechanism having at least two degrees of freedom, coupled to the first link and operable to move the first link with two degrees of freedom in a plane parallel to the plane of motion of the proximal link,
   wherein the second mechanism comprises one link or a serial connection of links connecting the base link to the first link, wherein the one link or the links of the serial connection is or are configured to move in a direction of instant motion which is different from a direction of instant motion of the proximal link, relative to the base link.

2. The apparatus of claim 1, wherein the second mechanism comprises at least two links connected in series to connect the base link to the first link through at least three rotational joints such that pivotal motion of the at least two links connected in series through the at least three rotational joints enables adjusting the length between the intermediate point and the proximal center of motion.

3. The apparatus of claim 2, wherein the at least two links connected in series are belt-driven links.

4. The apparatus of claim 2, wherein the second mechanism comprises an arrangement of links pivotally coupled between the base link and the first link, and configured to maintain at least two parallelograms having one side in common between each two parallelograms, wherein the arrangement of links comprises the at least two links connected in series.

5. The apparatus of claim 4, wherein one common side between two parallelograms is parallel to the first link.

6. The apparatus of claim 2, wherein the second mechanism comprises an arrangement of at least nine links including the base link and the first link which together form a set of three parallelograms, wherein the parallelograms are connected to one another via one link they have in common.

7. The apparatus of claim 1, wherein the second mechanism comprises two parallel links pivotally connecting the base link to the first link so as to maintain a parallelogram formed between the base link, the first link and the two parallel links, wherein the two parallel links have a different orientation relative to the base link compared to the proximal link, wherein each of the two parallel links comprise linear sliding joints between the base link and the first link.

8. The apparatus of claim 1, wherein the second mechanism comprises a pair of links arranged at a fixed and differing orientation to connect the base link to the first link, wherein the two links are configured for linear translation relative to the base link for moving the first link in the plane.

9. The apparatus of claim 8, wherein the pair of links are arranged orthogonally.

10. The apparatus of claim 1, wherein the second mechanism is configured to generate planar motion of the one link or serial connection of links connecting the base link to the first link.

11. The apparatus of claim 1, further comprising means to rotate the second mechanism, the base link, the proximal link and the distal link about an axis (A0) extending from the proximal center of motion to the remote center of motion.

12. The apparatus of claim 11, wherein the means to rotate comprises rotational joints pivotally coupling the base link to the mechanism base such that pivotal motion of the base link effects rotation about the axis extending from the proximal center of motion to the remote center of motion.

13. The apparatus of claim 1, wherein the distal link and the proximal links are straight links and wherein the parallelogram maintained by the first mechanism is maintained between the proximal link, the distal link, the first link and an axis extending from the proximal center of motion to the remote center of motion, wherein the distal link is parallel to the proximal link and the first link is parallel to an axis extending from the proximal center of motion to the remote center of motion.

14. The apparatus of claim 1, wherein the first mechanism comprises a second link parallel to the first link and pivotally coupled between the proximal link and the distal link in order to maintain the parallelogram between the orthogonal projections of the proximal center of motion, the distal center of motion, the intermediate point, and the remote point.

15. The apparatus of claim 1, wherein the proximal link is coupled to the proximal center of motion through a slide-rotary joint coupled to the base link, wherein the slide-rotary joint is adapted to allow the proximal link to slide in and out through the slide-rotary joint and to allow the proximal link to revolve about the proximal center of motion.

16. The apparatus of claim 15, wherein the slide-rotary joint is further configured for revolving about an axis extending from the proximal center of motion to the remote center of motion.

17. The apparatus of claim 1, wherein the second mechanism is coupled to the distal link through the first link only.

18. The apparatus of claim 1, comprising a third mechanism configured to adjust a position of the proximal center of motion relative to the base link independently of the second mechanism thereby adjusting a position of the remote center of motion.

19. The apparatus of claim 1, further comprising means to rotate a fourth linkage about an axis collinear to an axis of the proximal link, and means to transfer rotational motion of the fourth linkage to the distal link.

20. The apparatus of claim 1, wherein the first link is adjustable in length, so as to program a location of the remote center of motion with respect to the base link and so as to displace a workspace.

21. The apparatus according to claim 1, wherein the apparatus does not comprise any link or serial connection of links connecting the base link to the first link, which have a same direction of instant motion relative to the base link as the proximal link, when one disregards the distal link.

22. The apparatus according to claim 1, wherein the first link extends obliquely relative to an axis extending from the proximal center of motion to the remote center of motion, and wherein either one or both the first link and the distal link move in planes parallel to and offset from the plane of motion of the proximal link.

23. A method of operating the apparatus for generating motion around a remote center of motion, comprising:
positioning the remote center of motion by adjusting a position of a proximal center of motion relative to a base link thereby adjusting a position between a second mechanism and the proximal center of motion, wherein the apparatus for generating motion around the remote center of motion comprises:
 a distal link arranged to revolve about the remote center of motion and to translate through the remote center of motion;
 a proximal link arranged to revolve about the proximal center of motion through a rotational joint and a sliding joint to effect rotation about an axis of rotation comprising the proximal center of motion and to effect translation relative to the proximal center of motion in a plane of motion of the proximal link that is perpendicular to the axis of rotation;

the base link adapted to be coupled to a mounting fixture, wherein the proximal center of motion is coupled to the base link;
a first mechanism comprising a first link pivotally coupled to the proximal link and to the distal link, wherein pivotal coupling between the first link and the proximal link defines an intermediate point in constant relative relation to the first link and pivotal coupling between the first link and the distal link defines a remote point in constant relative relation to the first link, wherein the first mechanism is operable to transfer motion of the proximal link relative to the proximal center of motion to a motion of the distal link relative to the remote center of motion by maintaining a parallelogram between orthogonal projections of the proximal center of motion, the distal center of motion, the intermediate point, and the remote point on the plane of motion of the proximal link, wherein a length between the intermediate point and the proximal center of motion is adjustable;
the second mechanism having at least two degrees of freedom, coupled to the first link and operable to move the first link with two degrees of freedom in a plane parallel to the plane of motion of the proximal link,
wherein the second mechanism comprises one link or a serial connection of links connecting the base link to the first link, wherein the one link or the links of the serial connection is or are configured to have an orientation of instant motion which is different from an orientation of instant motion of the proximal link, relative to the base link.

* * * * *